United States Patent
Lin et al.

(10) Patent No.: US 8,318,667 B2
(45) Date of Patent: Nov. 27, 2012

(54) GLUCAGON RECEPTOR ANTAGONIST COMPOUNDS, COMPOSITIONS CONTAINING SUCH COMPOUNDS AND METHODS OF USE

(75) Inventors: Songnian Lin, Monroe, NJ (US); Libo Xu, Bridgewater, NJ (US); Edward Metzger, Somerset, NJ (US); Emma R. Parmee, Scotch Plains, NJ (US); Sheryl D. Debenham, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/202,124

(22) PCT Filed: Feb. 15, 2010

(86) PCT No.: PCT/US2010/024212
§ 371 (c)(1),
(2), (4) Date: Aug. 18, 2011

(87) PCT Pub. No.: WO2010/098994
PCT Pub. Date: Sep. 2, 2010

(65) Prior Publication Data
US 2011/0301082 A1   Dec. 8, 2011

Related U.S. Application Data

(60) Provisional application No. 61/155,314, filed on Feb. 25, 2009.

(51) Int. Cl.
*A61K 38/26* (2006.01)
*A61P 3/10* (2006.01)
*C07K 14/605* (2006.01)

(52) U.S. Cl. ........ 514/6.9; 514/7.2; 530/308; 530/389.2

(58) Field of Classification Search .................. None
See application file for complete search history.

(56) References Cited

U.S. PATENT DOCUMENTS

| | | | |
|---|---|---|---|
| 6,875,775 | B2 | 4/2005 | Sodervall at al. |
| 2005/0272794 | A1 | 12/2005 | Parmee et al. |
| 2006/0084681 | A1 | 4/2006 | Parmee et al. |
| 2007/0088071 | A1 | 4/2007 | Kim et al. |
| 2007/0105930 | A1 | 5/2007 | Parmee et al. |
| 2007/0203186 | A1 | 8/2007 | Beeson et al. |
| 2008/0085926 | A1 | 4/2008 | Stelmach et al. |
| 2008/0108620 | A1 | 5/2008 | Brockunier et al. |
| 2008/0153893 | A1 | 6/2008 | Gao et al. |
| 2008/0161347 | A1 | 7/2008 | Stelmach et al. |
| 2009/0054506 | A1 | 2/2009 | Liang et al. |
| 2009/0054662 | A1 | 2/2009 | Tan et al. |
| 2009/0105310 | A1 | 4/2009 | Kim et al. |
| 2009/0176854 | A1 | 7/2009 | Parmee et al. |
| 2009/0209564 | A1 | 8/2009 | Kim et al. |
| 2009/0215825 | A1 | 8/2009 | Parmee et al. |
| 2010/0144824 | A1 | 6/2010 | Stelmach et al. |
| 2011/0065634 | A1 | 3/2011 | Greenlee et al. |
| 2011/0172256 | A1 | 7/2011 | Lin et al. |
| 2011/0178007 | A1 | 7/2011 | Stamford et al. |
| 2011/0251248 | A1 | 10/2011 | Lin et al. |
| 2011/0281795 | A1 | 11/2011 | Lin et al. |
| 2011/0306624 | A1 | 12/2011 | Lin et al. |
| 2011/0312911 | A1 | 12/2011 | Kats-Kagan et al. |
| 2012/0010262 | A1 | 1/2012 | Chung et al. |

FOREIGN PATENT DOCUMENTS

| | | |
|---|---|---|
| WO | 2010/080971 | 7/2010 |
| WO | 2010/144664 | 12/2010 |
| WO | 2011/037815 | 3/2011 |
| WO | 2011/119541 | 9/2011 |
| WO | 2011/119559 | 9/2011 |

OTHER PUBLICATIONS

Int'l Search Report of PCT/US2010/24212, dated Apr. 1, 2010.

*Primary Examiner* — Julie Ha
*Assistant Examiner* — Li Ni Komatsu
(74) *Attorney, Agent, or Firm* — Anna L. Cocuzzo; John C. Todaro

(57) ABSTRACT

Glucagon receptor antagonist compounds are disclosed. The compounds are useful for treating type (2) diabetes and related conditions. Pharmaceutical compositions and methods of treatment are also included.

20 Claims, No Drawings

GLUCAGON RECEPTOR ANTAGONIST COMPOUNDS, COMPOSITIONS CONTAINING SUCH COMPOUNDS AND METHODS OF USE

BACKGROUND OF THE INVENTION

The present invention relates to glucagon receptor antagonist compounds, compositions containing such compounds and various methods of treatment relating to type 2 diabetes mellitus and related conditions.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level >126 mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure >130/80 mmHg in a resting state), nephropathy, neuropathy and retinopathy.

Patients having type 2 diabetes mellitus characteristically exhibit elevated plasma insulin levels compared with nondiabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by alpha cells in pancreatic islets in response to falling blood glucose levels. The hormone binds to specific receptors in liver cells that trigger glycogenolysis and an increase in gluconeogenesis through cAMP-mediated events. These responses generate glucose (e.g. hepatic glucose production) to help maintain euglycemia by preventing blood glucose levels from falling significantly. In addition to elevated levels of circulating insulin, type 2 diabetics have elevated levels of plasma glucagon and increased rates of hepatic glucose production. Antagonists of the glucagon receptor are useful in improving insulin responsiveness in the liver, decreasing the rate of gluconeogenesis and glycogenolysis, and lowering the rate of hepatic glucose output resulting in a decrease in the levels of plasma glucose.

SUMMARY OF THE INVENTION

The present invention relates to a compound represented by formula I:

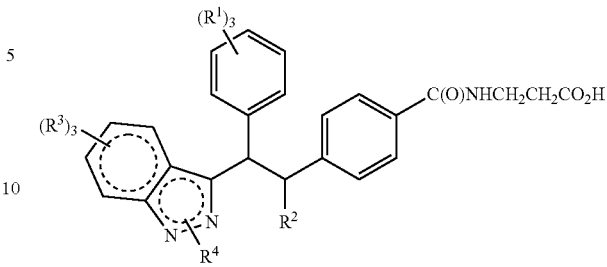

or a pharmaceutically acceptable salt or solvate thereof wherein:

each $R^1$ represents H or is selected from the group consisting of: halo, CN, OH, $NO_2$, $CO_2R^a$, $NR^aR^b$, $S(O)_pR^a$, $C_{1-10}$alkyl, $C_{2-10}$alkenyl or $C_{1-10}$alkoxy, the alkyl and alkenyl portions of $C_{1-10}$alkyl, $C_{2-10}$alkenyl and $C_{1-10}$alkoxy being optionally substituted with 1-5 halo atoms up to perhalo; and further optionally substituted with 1 group selected from OH, oxo and $C_{1-6}$alkoxy;

p represents 0, 1 or 2;

each $R^a$ and $R^b$ independently represents H or $C_{1-4}$alkyl optionally substituted with 1-5 halo atoms up to perhalo; and further optionally substituted with 1 group selected from OH, oxo and $C_{1-6}$alkoxy;

$R^2$ represents $C_{1-6}$alkyl or $C_{2-6}$alkenyl, each optionally substituted with 1-5 halo atoms up to perhalo, and further optionally substituted with 1 group selected from OH, oxo and $C_{1-6}$alkoxy;

each $R^3$ represents H or halo, or 1-2 $R^3$ groups represent H or halo and the remainder represent a member selected from the group consisting of: CN; OH; $NO_2$; $CO_2R^a$; $NR^aR^b$; $S(O)_pR^a$; phenyl or 5-6 membered heteroaryl containing 1-3 nitrogen atoms and 0-1 oxygen or sulfur atom, said phenyl and heteroaryl being optionally substituted with 1-3 halo atoms and 1-2 members selected from the group consisting of $S(O)_pR^a$, $C_{1-3}$alkyl, $C_{1-3}$alkoxy, $haloC_{1-3}$alkyl and $haloC_{1-3}$alkoxy; $C_{1-10}$alkyl; $C_{2-10}$alkenyl and $C_{1-10}$alkoxy, the alkyl and alkenyl portions of $C_{1-10}$alkyl, $C_{2-10}$alkenyl and $C_{1-10}$alkoxy being optionally substituted with 1-5 halo atoms up to perhalo; and further optionally substituted with 1 group selected from OH, oxo, $NR^aR^b$, and $C_{1-6}$alkoxy;

and $R^4$ represents H or is selected from the group consisting of: $C_{1-4}$alkyl, $haloC_{1-4}$alkyl and phenyl optionally substituted with 1-3 halo groups and 1-2 $C_{1-3}$alkyl, $haloC_{1-3}$alkyl, $OC_{1-3}$alkyl and $haloOC_{1-3}$alkyl groups.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. Examples of cycloalkyl include cyclopropyl, cyclobutyl, cyclopentyl, cyclohexyl, cycloheptyl, decahydronaphthyl and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like. Cycloalkenyl is a subset of alkenyl. If no number is specified, 4-8 carbon atoms are included. Examples include cyclopentenyl, cyclohexenyl and the like.

"Aryl" (Ar) means mono- and bicyclic aromatic rings containing 6-12 carbon atoms. Examples of aryl include phenyl, naphthyl, indenyl and the like. "Aryl" also includes monocyclic rings fused to an aryl group. Examples include tetrahydronaphthyl, indanyl and the like.

"Heteroaryl" (HAR) means a mono- or bicyclic aromatic ring or ring system containing at least one heteroatom selected from O, S and N, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

"Halogen" (Halo) includes fluorine, chlorine, bromine and iodine. The terms "haloalkyl", "haloalkoxy" and the like refer to halogenated alkyl and alkoxy groups of the size specified, substituted with 1-5 halo atoms, up to perhalo, and preferably from 1-3 halo atoms selected from fluoro and chloro. For example, haloC$_{1-6}$alkyl refers to a C$_{1-6}$alkyl group substituted with 1 to 5 halo atoms, up to perhalo.

One aspect of the invention that is of interest relates to a compound represented by formula I:

I

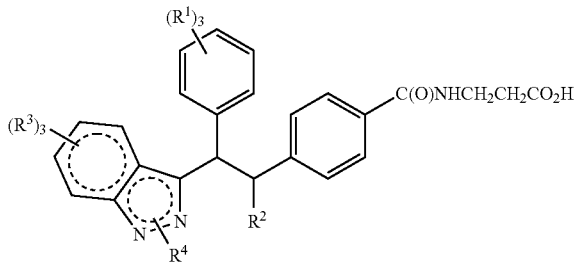

or a pharmaceutically acceptable salt or solvate thereof wherein:

each R$^1$ represents H or is selected from the group consisting of: halo, CN, OH, NO$_2$, CO$_2$R$^a$, NR$^a$R$^b$, S(O)$_p$R$^a$, C$_{1-10}$alkyl, C$_{2-10}$alkenyl or C$_{1-10}$alkoxy, the alkyl and alkenyl portions of C$_{1-10}$alkyl, C$_{2-10}$alkenyl and C$_{1-10}$alkoxy being optionally substituted with 1-5 halo atoms up to perhalo; and further optionally substituted with 1 group selected from OH, oxo and C$_{1-6}$alkoxy;

p represents 0, 1 or 2;

each R$^a$ and R$^b$ independently represents H or C$_{1-4}$alkyl optionally substituted with 1-5 halo atoms up to perhalo; and further optionally substituted with 1 group selected from OH, oxo and C$_{1-6}$alkoxy;

R$^2$ represents C$_{1-6}$alkyl or C$_{2-6}$alkenyl, each optionally substituted with 1-5 halo atoms up to perhalo, and further optionally substituted with 1 group selected from OH, oxo and C$_{1-6}$alkoxy;

each R$^3$ represents H or halo, or 1-2 R$^3$ groups represent H or halo and the remainder represent a member selected from the group consisting of: CN; OH; NO$_2$; CO$_2$R$^a$; NR$^a$R$^b$; S(O)$_p$R$^a$; phenyl or 5-6 membered heteroaryl containing 1-3 nitrogen atoms and 0-1 oxygen or sulfur atom, said phenyl and heteroaryl being optionally substituted with 1-3 halo atoms and 1-2 members selected from the group consisting of: S(O)$_p$R$^a$, C$_{1-3}$alkyl, C$_{1-3}$alkoxy, haloC$_{1-3}$alkyl and haloC$_{1-3}$alkoxy; C$_{1-10}$alkyl; C$_{2-10}$alkenyl and C$_{1-10}$alkoxy, the alkyl and alkenyl portions of C$_{1-10}$alkyl, C$_{2-10}$alkenyl and C$_{1-10}$alkoxy being optionally substituted with 1-5 halo atoms up to perhalo; and further optionally substituted with 1 group selected from OH, oxo, NR$^a$R$^b$, and C$_{1-6}$alkoxy;

and R$^4$ represents H or is selected from the group consisting of C$_{1-4}$alkyl, haloC$_{1-4}$alkyl and phenyl optionally substituted with 1-3 halo groups and 1-2 C$_{1-3}$alkyl, haloC$_{1-3}$alkyl, OC$_{1-3}$alkyl and haloOC$_{1-3}$alkyl groups.

One aspect of the invention that is of interest relates to a compound of formula I-a:

I-a

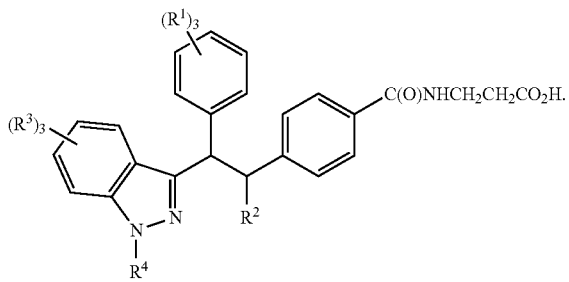

Another aspect of the invention that is of interest relates to a compound of formula I-b:

I-b

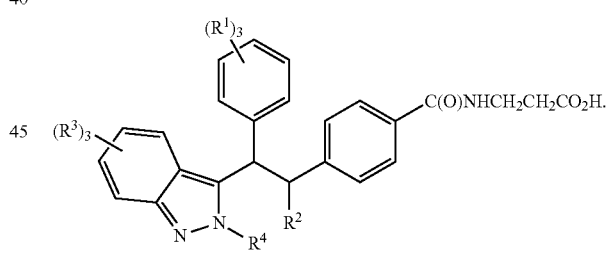

Another aspect of the invention that is of interest relates to a compound in accordance with formula I-c:

I-c

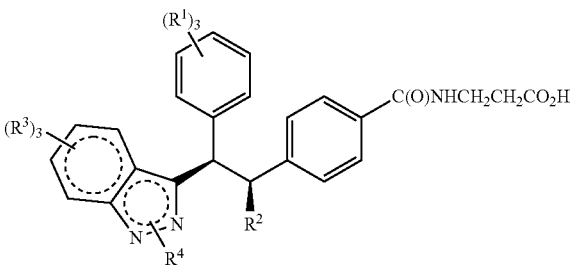

Another aspect of the invention that is of interest relates to a compound represented by formula I, or a pharmaceutically acceptable salt or solvate thereof, wherein;

each $R^1$ represents H or is selected from the group consisting of halo, CN, $C_{1-10}$alkyl, or $C_{1-10}$alkoxy, the alkyl portions of $C_{1-10}$alkyl, and $C_{1-10}$alkoxy being optionally substituted with 1-5 halo atoms up to perhalo; and further optionally substituted with 1 group selected from OH, oxo and $C_{1-6}$alkoxy.

Another aspect of the invention that is of interest relates to a compound represented by formula I, or a pharmaceutically acceptable salt or solvate thereof, wherein:

each $R^1$ represents H or is selected from the group consisting of: halo selected from chloro and fluoro, CN, $C_{1-4}$alkyl, or $C_{1-4}$alkoxy, the alkyl portions of $C_{1-4}$alkyl, and $C_{1-4}$alkoxy being optionally substituted with 1-3 halo atoms selected from chloro and fluoro; and further optionally substituted with 1 group selected from OH and $OCH_3$.

Another aspect of the invention that is of interest relates to a compound represented by formula I, or a pharmaceutically acceptable salt or solvate thereof, wherein:

each $R^1$ represents H or is selected from the group consisting of: halo selected from chloro and fluoro, and CN.

Another aspect of the invention that is of interest relates to a compound represented by formula I, or a pharmaceutically acceptable salt or solvate thereof, wherein:

$R^2$ represents $C_{1-3}$alkyl or $C_{2-4}$alkenyl, each optionally substituted with 1-3 halo atoms selected from chloro and fluoro, and further optionally substituted with 1 group selected from OH, oxo and $OCH_3$.

Another aspect of the invention that is of interest relates to a compound represented by formula I, or a pharmaceutically acceptable salt or solvate thereof, wherein:

$R^2$ represents n-propyl or allyl, each optionally substituted with 1-3 halo atoms selected from chloro and fluoro.

Another aspect of the invention that is of interest relates to a compound represented by formula I, or a pharmaceutically acceptable salt or solvate thereof, wherein:

$R^2$ represents n-propyl or allyl.

Another aspect of the invention that is of interest relates to a compound represented by formula I, or a pharmaceutically acceptable salt or solvate thereof, wherein:

each $R^3$ represents H or halo, or 1-2 $R^3$ groups represent H or halo and the remainder represent a member selected from the group consisting of: CN; $S(O)_p R^a$; phenyl or 5-6 membered heteroaryl containing 1-3 nitrogen atoms and 0-1 oxygen or sulfur atom, said phenyl and heteroaryl being optionally substituted with 1-3 halo atoms and 1-2 members selected from the group consisting of: $S(O)_p R^a$, $C_{1-3}$alkyl, $C_{1-3}$alkoxy, halo$C_{1-3}$alkyl and halo$C_{1-3}$alkoxy; $C_{1-10}$alkyl and $C_{1-10}$alkoxy, the alkyl portions of $C_{1-10}$alkyl and $C_{1-10}$alkoxy being optionally substituted with 1-3 halo atoms up to perhalo, p is 0 or 2, and $R^a$ is H or $C_{1-4}$alkyl optionally substituted with 1-3 halo atoms.

Another aspect of the invention that is of interest relates to a compound represented by formula I, or a pharmaceutically acceptable salt or solvate thereof, wherein:

each $R^3$ represents H or halo selected from chloro, fluoro and bromo, or 1-2 $R^3$ groups represent H or halo selected from chloro, fluoro and bromo, and the remainder represent a member selected from the group consisting of: CN; $C_{1-4}$alkyl and $C_{1-4}$alkoxy, the alkyl and portions of $C_{1-4}$alkyl and $C_{1-4}$alkoxy being optionally substituted with 1-3 halo atoms selected from chloro and fluoro; $SO_2C_{1-4}$alkyl; phenyl or 5-6 membered heteroaryl containing 1-2 nitrogen atoms, said phenyl and heteroaryl being optionally substituted with 1-3 halo atoms selected from chloro, fluoro and bromo, and 1 member selected from the group consisting of: $SO_2C_{1-3}$alkyl, $C_{1-3}$alkyl, $C_{1-3}$alkoxy, halo$C_{1-3}$alkyl and halo$C_{1-3}$alkoxy.

Another aspect of the invention that is of interest relates to a compound represented by formula I, or a pharmaceutically acceptable salt or solvate thereof, wherein:

each $R^3$ represents H or halo selected from chloro and fluoro, or 1-2 $R^3$ groups represent H or halo selected from chloro and fluoro, and the remainder represent a member selected from the group consisting of: bromo, $CH_3$, $CF_3$, CN; phenyl or pyridyl, said phenyl and pyridyl being optionally substituted with 1-2 halo atoms selected from chloro and fluoro, and 1 member selected from the group consisting of: $CH_3$, $OCH_3$, $CF_3$, $OCF_3$, and $SO_2CH_3$.

Another aspect of the invention that is of interest relates to a compound represented by formula I, or a pharmaceutically acceptable salt or solvate thereof, wherein:

$R^4$ represents H or is selected from the group consisting of $C_{1-3}$alkyl, halo$C_{1-3}$alkyl and phenyl optionally substituted with 1-3 halo groups selected from chloro and fluoro, and 1-2 $C_{1-2}$alkyl, $CF_3$, $OCH_3$ and $OCF_3$ groups.

A subset of the invention that is of particular interest relates to a compound represented by formula I:

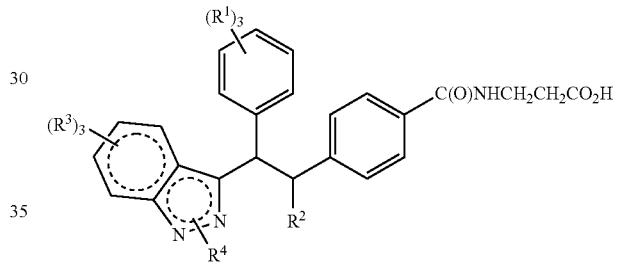

or a pharmaceutically acceptable salt or solvate thereof, wherein:

each $R^1$ represents H or is selected from the group consisting of: halo, CN, $C_{1-10}$alkyl, or $C_{1-10}$alkoxy, the alkyl portions of $C_{1-10}$alkyl, and $C_{1-10}$alkoxy being optionally substituted with 1-5 halo atoms up to perhalo; and further optionally substituted with 1 group selected from OH, oxo and $C_{1-6}$alkoxy;

$R^2$ represents $C_{1-3}$alkyl or $C_{2-4}$alkenyl, each optionally substituted with 1-3 halo atoms selected from chloro and fluoro, and further optionally substituted with 1 group selected from OH, oxo and $OCH_3$, each $R^3$ represents H or halo, or 1-2 $R^3$ groups represent H or halo and the remainder represent a member selected from the group consisting of: CN; $S(O)_p R^a$; phenyl or 5-6 membered heteroaryl containing 1-3 nitrogen atoms and 0-1 oxygen or sulfur atom, said phenyl and heteroaryl being optionally substituted with 1-3 halo atoms and 1-2 members selected from the group consisting of: $S(O)_p R^a$, $C_{1-3}$alkyl, $C_{1-3}$alkoxy, halo$C_{1-3}$alkyl and halo$C_{1-3}$alkoxy; $C_{1-10}$alkyl and $C_{1-10}$alkoxy, the alkyl portions of $C_{1-10}$alkyl and $C_{1-10}$alkoxy being optionally substituted with 1-3 halo atoms up to perhalo, p is 0 or 2, and $R^a$ is H or $C_{1-4}$alkyl optionally substituted with 1-3 halo atoms, and $R^4$ represents H or is selected from the group consisting of: $C_{1-3}$alkyl, halo$C_{1-3}$alkyl and phenyl optionally substituted with 1-3 halo groups selected from chloro and fluoro, and 1-2 $C_{1-2}$alkyl, $CF_3$, $OCH_3$ and $OCF_3$ groups.

Examples of compounds that fall within the invention described herein are in the tables and examples contained herein. Pharmaceutically acceptable salts and solvates of the compounds disclosed in the tables are included as well.

Another aspect of the invention that is of interest relates to a pharmaceutical composition comprising a compound as described above with respect to formula I or a pharmaceutically acceptable salt or solvate thereof in combination with a pharmaceutically acceptable carrier.

Another aspect of the invention that is of interest relates to a method of treating type 2 diabetes mellitus in a mammalian patient in need of such treatment comprising administering to said patient a compound as described above with respect to formula I or a pharmaceutically acceptable salt or solvate thereof in an amount that is effective to treat type 2 diabetes mellitus.

Another aspect of the invention that is of interest relates to a method of delaying the onset of type 2 diabetes mellitus in a mammalian patient in need thereof comprising administering to the patient a compound as described above in accordance with formula I or a pharmaceutically acceptable salt or solvate thereof in an amount that is effective to delay the onset of type 2 diabetes mellitus.

Another aspect of the invention that is of interest relates to a method of treating hyperglycemia, diabetes or insulin resistance in a mammalian patient in need of such treatment which comprises administering to said patient a compound as described above in accordance with formula I or a pharmaceutically acceptable salt or solvate thereof in an amount that is effective to treat hyperglycemia, diabetes or insulin resistance.

Another aspect of the invention that is of interest relates to a method of treating non-insulin dependent diabetes mellitus in a mammalian patient in need of such treatment comprising administering to the patient an anti-diabetic effective amount of a compound in accordance with formula I or a pharmaceutically acceptable salt or solvate thereof as described above.

Another aspect of the invention that is of interest relates to a method of treating obesity in a mammalian patient in need of such treatment comprising administering to said patient a compound in accordance with formula I as described above or a pharmaceutically acceptable salt or solvate thereof in an amount that is effective to treat obesity.

Another aspect of the invention that is of interest relates to a method of treating Syndrome X in a mammalian patient in need of such treatment, comprising administering to said patient a compound in accordance with formula I as described above or a pharmaceutically acceptable salt or solvate thereof in an amount that is effective to treat Syndrome X.

Another aspect of the invention that is of interest relates to a method of treating a lipid disorder selected from the group consisting of: dyslipidemia, hyperlipidemia, hypertriglyceridemia, hypercholesterolemia, low HDL and high LDL in a mammalian patient in need of such treatment, comprising administering to said patient a compound as described above with respect to formula T or a pharmaceutically acceptable salt or solvate thereof in an amount that is effective to treat said lipid disorder.

Another aspect of the invention that is of interest relates to a method of treating atherosclerosis in a mammalian patient in need of such treatment, comprising administering to said patient a compound in accordance with formula I as described above or a pharmaceutically acceptable salt or solvate thereof in an amount effective to treat atherosclerosis.

Another aspect of the invention that is of interest relates to a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with formula I as described above or a pharmaceutically acceptable salt or solvate thereof in an amount that is effective to treat said condition.

Another aspect of the invention that is of interest relates to a method of delaying the onset of a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound in accordance with formula I as described above or a pharmaceutically acceptable salt or solvate thereof in an amount that is effective to delay the onset of said condition.

Another aspect of the invention that is of interest relates to a method of reducing the risk of developing a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I as described above or a pharmaceutically acceptable salt or solvate thereof in an amount that is effective to reduce the risk of developing said condition.

Another aspect of the invention that is of interest relates to a method of treating a condition selected from the group consisting of:

(1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (1.3) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient effective amounts of a compound of formula I as described above, or a pharmaceutically acceptable salt or solvate thereof, and another compound that is selected from the list provided below.

(1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO097/29079, WO99/02499, WO 01/58869, WO 01/64632, WO 01/64633, WO 01/64634, WO02/076949, WO 03/007887, WO 04/048317, and WO 05/000809; and EPO Application No. EP-658546, EP-656354, EP-576357; (4) anti-obesity serotonergic agents, such as fenfluramine, dexfenfluramine, phentermine, and sibutramine; (5) J33-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A, and such as those disclosed in U.S. Pat. No. 5,705,515, and U.S. Pat. No. 5,451,677 and PCT Patent Publications WO94/18161, WO95/29159, WO97/46556, WO98/04526 and W098/32753, WO 01/74782, and WO 02/32897; (6) pancreatic lipase inhibitors, such as orlistat (Xenical®), cetilistat, Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, hereby incorporated by reference in their entirety; European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hounone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027, and Japanese Patent Application Nos. JP 13226269, and JP 2004-139909; (11) melanin-concentrating hormone 2 receptor (MCH2R) agonist/antagonists; (12) orexin-1 receptor antagonists, such as SB-334867-A, and those disclosed in PCT Patent Application Nos. WO 01/96302, WO 01/68609, WO 02/51232, and WO 02/51838; (13) serotonin reuptake inhibitors such as fluoxetine, paroxetine, and sertraline, and those disclosed in U.S. Pat. No. 6,365,633, and PCT Patent Application Nos. WO 01/27060 and WO 01/162341; (14) melanocortin agonists, such as Melanotan II, CHIR86036 (Chiron), ME-10142, and ME-10145 (Melacure), CHIR86036 (Chiron); PT-141, and PT-14 (Palatin); (15) other MC4R (melanocortin 4 receptor) agonists, such as those disclosed in: U.S. Pat. Nos. 6,410,548; 6,294,534; 6,350,760; 6,458,790; 6,472,398; 6,376,509; and 6,818,658; US Patent Publication No. US2002/0137664; US2003/0236262; US2004/009751; US2004/0092501; and PCT Application Nos. WO 99/64002; WO 00/74679; WO 01/70708; WO 01/70337; WO 01/74844; WO 01/91752; WO 01/991752; WO 02/15909; WO 02/059095; WO 02/059107; WO 02/059108; WO 02/059117; WO 02/067869; WO 02/068387; WO 02/068388; WO 02/067869; WO 02/11715; WO 02/12166; WO 02/12178; WO 03/007949; WO 03/009847; WO 04/024720; WO 04/078716; WO 04/078717; WO 04/087159; WO 04/089307; and WO 05/009950; (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-1 agonists (cholecystokinin-A) agonists, such as AR-R 15849, GI 181771, JMV-180, A-71378, A-71623 and SR146131, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and those described and disclosed in PCT Application No. WO 02/15905, and O-[3-(1H-imidazol-4-yl)propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (25) β-hydroxy steroid dehydrogenase-1 inhibitors (β-HSD-1); (26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos, WO 01/87335, and WO 02/08250; (30) leptin, including recombinant human leptin (PEG-OB, Hoffman La Roche) and recombinant methionyl human leptin (Amgen); (31) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (32) other BRS3 (bombesin receptor subtype 3) agonists such as [D-Phe6, beta-Ala11, Phe13, Nle14]Bn(6-14) and [D-Phe6, Phe13]Bn(6-13)propylamide, and those compounds disclosed in Pept. Sci. 2002

August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron), and those disclosed in PCT Application Nos. WO 94/09134, WO 98/22128, and WO 99/43813; (35) monoamine reuptake inhibitors, such as sibutramine, and those disclosed in U.S. Pat. Nos. 4,746,680, 4,806,570, and 5,436,272, U.S. Patent Publication No. 2002/0006964 and PCT Application Nos. WO 01/27068, and WO 01/62341;

(36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (37) thyroid hormone β agonists, such as KB-2611 (KaroBioBMS), and those disclosed in PCT Application No. WO 02/15845, and Japanese Patent Application No. JP 2000256190; (38) FAS (fatty acid synthase) inhibitors, such as Cerulenin and C75;

(39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444 and sitagliptin; and the compounds disclosed in U.S. Pat. No. 6,699,871, which is incorporated herein by reference; and International Patent Application Nos. WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (45) dicarboxylate transporter inhibitors; (46) glucose transporter inhibitors; (47) phosphate transporter inhibitors; (48) Metformin (Glucophage®); (49) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)), and those disclosed in U.S. Pat. No. 5,026,685, U.S. Pat. No. 5,604,203, U.S. Pat. No. 5,574,010, U.S. Pat. No. 5,696,093, U.S. Pat. No. 5,936,092, U.S. Pat. No. 6,046,162, U.S. Pat. No. 6,046,167, U.S. Pat. No. 6,093,692, U.S. Pat. No. 6,225,445, U.S. Pat. No. 5,604,203, U.S. Pat. No. 4,002,531, U.S. Pat. No. 4,179,337, U.S. Pat. No. 5,122,614, U.S. Pat. No. 5,349,052, U.S. Pat. No. 5,552,520, U.S. Pat. No. 6,127,355, WO 95/06058, WO 98/32466, WO 03/026591, WO 03/057235, WO 03/027637, and WO 2004/066966; (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-6)-pNPY; (52) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (53) cyclooxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (54) Neuropeptide Y1 (NPY1) antagonists such as BIBP3226, J-115814, BIBO 3304, LY-357897, CP-671906, GI-264879A and those disclosed in U.S. Pat. No. 6,001,836; and PCT Application Nos. WO 96/14307, WO 01/23387, WO 99/51600, WO 01/85690, WO 01/85098, WO 01/85173, and WO 01/89528; (55) Opioid antagonists such as nalmefene (Revex®), 3-methoxynaltrexone, naloxone, naltrexone, and those disclosed in: PCT Application No. WO 00/21509; (57) 11β HSD-1 (11-beta hydroxy steroid dehydrogenase type 1) inhibitors such as BVT 3498, BVT 2733, and those disclosed in WO 01/90091, WO 01/90090, WO 01/90092, and U.S. Pat. No. 6,730,690 and US Publication No. US 2004-0133011, which are incorporated by reference herein in their entirety; (56) aminorex; (57) amphechloral; (58) amphetamine; (59) benzphetamine; (60) chlorphentermine; (61) clobenzorex; (62) cloforex; (63) clominorex; (64) clortermine; (65) cyclexedrine; (66) dextroamphetamine; (67) diphemethoxidine, (68) N-ethylamphetamine; (69) fenbutrazate; (70) fenisorex; (71) fenproporex; (72) fludorex; (73) fluminorex; (74) furfurylmethylamphetamine; (75) levamfetamine; (76) levophacetoperane; (77) mefenorex; (78) metamfepramone; (79) methamphetamine; (80) norpseudoephedrine; (81) pentorex; (82) phendimetrazine; (83) phenmetrazine; (84) picilorex; (85) phytopharm 57; (86) zonisamide, (87) neuromedin U and analogs or derivatives thereof, (88) oxyntomodulin and analogs or derivatives thereof,

(89) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699; (90) Qnexa; (91) smoking cessation agents, such as nicotine agonists, partial nicotine agonists, such as varenicline, monoamine oxidase inhibitors (MAOIs), antidepressants such as bupropion, doxepine, and nortriptyline; and anxiolytic agents such as buspirone or clonidine.

Specific compounds of use in combination with a compound of the present invention include: simvastatin, mevastatin, ezetimibe, atorvastatin, sitagliptin, metformin, sibutramine, orlistat, Qnexa, topirarnate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl){3-[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1-yl}methyl)benzonitrile, 3-((4-chlorophenyl){3-[1-(3,5-difluorophenyl)-2,2-dimethylpropyl]azetidin-1-yl}methyl) benzonitrile, 3-((1S)-1-{1-[(S)-(3-cyanophenyl)(4-cyanophenyl)methyl]azetidin-3-yl}-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl){3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl) methyl]benzonitrile, 3-[(S)-(3-{(1S)-1-[3-(5-amino-1,3,4-oxadiazol-2-yl)-5-fluorophenyl]-2-fluoro-2- methylpropyl}azetidin-1-yl)(4-chlorophenyl)methyl]benzonitrile, 3-[(5)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl)methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl)azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl]benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl]methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,2,4-oxadiazol-3-yl)phenyl]methyl}azetidin-3-yl)-2-fluoro-2-methylpropyl]-5-fluorobenzonitrile, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl]azetidin-1-yl}[3-(5-oxo-4,5-dihydro-1,3,4-oxadiazol-2-yl)phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H), 4'-piperidine]-1'-carboxamide, 3-oxo-N-(7-trifluoromethylpyrido[3,2-b]pyridin-2-yl)spiro-[isobenzofuran-1(3H), 4'-piperidine]-1'-carboxamide, N-[5-(3-fluorophenyl)-2-pyrimidinyl]-3-oxospiro-[isobenzofuran-1(3H), 4'-piperidine]-1'-carboxamide, trans-3'-oxo-N-(5-phenyl-2-pyrimidinyl)spiro[cyclohexane-1,1'(3H)-isohenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1(3H), 1'-cyclohexane]-4'-carboxamide, trans-N-[5-(3-fluorophenyl)-2-pyrimidinyl]-3-oxospiro[5-azaisobenzofuran-1(3H), 1'-cyclohexane]-4'-carboxamide, trans-N-[5-(2-fluorophenyl)-2-pyrimidinyl]-3-oxospiro[5-azaisobenzofuran-1(3H), 1'-cyclohexane]-4'-carboxamide, trans-N-[1-(3,5-difluorophenyl)-4-imidazolyl]-3-oxospiro[7-azaisobenzofuran-1(3H), 1'-cyclohexane]-4'-carboxamide, trans-3-oxo-N-(1-phenyl-4-pyrazolyl)spiro[4-azaisobenzofuran-1(3H), 1'-cyclohexane]-4'-carboxamide, trans-N-[1-(2-fluorophenyl)-3-pyrazolyl]-3-oxospiro[6-azaisobenzofuran-1(3H), 1'-cyclohexane]-4'-carboxamide, trans-3-oxo-N-(1-phenyl-3-pyrazolyl)spiro[6-azaisobenzofuran-1(3H), 1'-cyclohexane]-4'-carboxamide, trans-3-oxo-N-(2-phenyl-1,2,3-triazol-4-yl)spiro[6-azaisobenzofuran-1(3H), 1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl)spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro[chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro[chroman-2,4'-piperidin]-4-one; and pharmaceutically acceptable salts and esters thereof. Specific MCH1R antagonist compounds of use in combination with a compound of the present invention include: 1-{(4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1H)-one, or a pharmaceutically acceptable salt thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl]propoxy}phenyl)pyrido[2,3-d]pyrimidin-4(3H)-one 2-methyl-3-(4-{3-[(3S)-3-methylpiperidin-1-yl]propoxy}phenyl)pyrido[4,3-d]pyrimidin-4(3H)-one, 3-{4-

[(1-cyclobutyl-4-piperidinyl)oxy]phenyl}-2,5-dimethyl-4 (3H)-quinazolinone, 3-{4-[(1-cyclobutyl-4-piperidinyl)oxy] phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4 (3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4,3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy] phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy] phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl) propoxy]phenyl}-4(3H)-quinazolinone, 5-methoxy-2-methyl-3-(4-{3-[(3S)-3-methylpiperidin-1-yl] propoxy}phenyl)-4(3H)-quinazolinone, 7-methoxy-2-methyl-3-(4-{3-[(3S)-3-methylpiperidin-1-yl] propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl] propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl] carbonyl}-1-piperazinyl)-1-naphthoic acid; 3-(4-{[1-(3-ethoxyphenyl)-2-(4-fluorophenyl)-1H-imidazol-4-yl] carbonyl}-1-piperazinyl)-1-naphthoic acid; 3-(4-{[1-(3-ethoxyphenyl)-2-(2,4-difluorophenyl)-1H-imidazol-4-yl] carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5 R)-1'-{[3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl) ethyl]-5H-spiro[furo[3,4-b]pyridine-7,4'-piperidine]; 3) 2-(1'-{[(3S,4S)-1-tert-butyl-4-(2,4-difluorophenyl)pyrrolidin-3-yl]carbonyl}-3-chloro-2-methyl-5H-spiro[furo[3,4-b] pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl)ethyl]-1'H, 5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methylpropane-nitrile; and pharmaceutically acceptable salts thereof. Still further, neurokinin-1 (NK-1) receptor antagonists may be favorably employed in combination with a compound of the present invention. NK-1 receptor antagonists of use in the present invention are fully described in the art. Specific neurokinin-1 receptor antagonists of use in the present invention include: (±)-(2R3R,2S3S)—N-{[2-cyclopropoxy-5-(trifluoromethoxy)-phenyl]methyl}-2-phenylpiperidin-3-amine; 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; aprepitant; CJ17493; GW597599; GW679769; R673; RO67319; R1124; R1204; SSR146977; SSR240600; T-2328; and T2763; or a pharmaceutically acceptable salts thereof. Examples of other anti-obesity agents that can be employed in combination with a compound of formula I are disclosed in "Patent focus on new anti-obesity agents," *Exp. Opin. Ther. Patents*, 10: 819-831 (2000); "Novel anti-obesity drugs," *Exp. Opin. Invest. Drugs*, 9: 1317-1326 (2000); and "Recent advances in feeding suppressing agents: potential therapeutic strategy for the treatment of obesity, *Exp. Opin. Ther. Patents*, 11: 1677-1692 (2001). The role of neuropeptide Y in obesity is discussed in *Exp. Opin. Invest. Drugs*, 9: 1327-1346 (2000). Cannabinoid receptor ligands are discussed in *Exp. Opin. Invest. Drugs*, 9: 1553-1571 (2000).

Another aspect of the invention that is of interest relates to a method of treating a condition selected from the group consisting of: hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor.

More particularly, another aspect of the invention that is of interest relates to a method of treating a condition selected from the group consisting of: hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor wherein the HMG-CoA reductase inhibitor is a statin.

Even more particularly, another aspect of the invention that is of interest relates to a method of treating a condition selected from the group consisting of: hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor, wherein the HMG CoA reductase inhibitor is a statin selected from the group consisting of: lovastatin, simvastatin, pravastatin, fluvastatin, atorvastatin, itavastatin, rosuvastatin and rivastatin.

Another aspect of the invention that is of interest relates to a method of reducing the risk of developing a condition selected from the group consisting of: hypercholesterolemia, atherosclerosis, low HDL levels, high LDL levels, hyperlipidemia, hypertriglyceridemia and dyslipidemia, and the sequelae of such conditions, delaying the onset or reducing the risk of developing said condition, comprising administering to a mammalian patient in need of such treatment therapeutically effective amounts of a compound of formula I as described above and an HMG-CoA reductase inhibitor.

More particularly, another aspect of the invention that is of interest relates to a method for delaying the onset of, or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin, and even more particularly, a statin selected from the group consisting of: lovastatin, simvastatin, pravastatin, fluvastatin, atorvastatin, itavastatin, rosuvastatin and rivastatin.

Yet even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is simvastatin, atorvastatin or rosuvastatin.

Another aspect of the invention that is of interest relates to a method for delaying the onset or reducing the risk of developing atherosclerosis in a human patient in need of such treatment comprising administering to said patient effective amounts of a compound of formula as described above and a cholesterol absorption inhibitor. More particularly, another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor wherein the cholesterol absorption inhibitor is ezetimibe.

Another aspect of the invention that is of interest relates to a method for delaying the onset or reducing the risk of developing the other diseases and conditions mentioned above, in a mammalian patient in need of such treatment comprising administering to said patient effective amounts of a compound of formula I as described above, and a cholesterol absorption inhibitor.

More particularly, another aspect of the invention that is of interest relates to a method for delaying the onset or reducing the risk of developing the other diseases and conditions mentioned above, in a human patient in need of such treatment comprising administering to said patient effective amounts of a compound of formula I as described above, and a cholesterol absorption inhibitor, wherein the cholesterol absorption inhibitor is ezetimibe.

Another aspect of the invention that is of interest relates to a method of treating, delaying the onset, or preventing a condition selected from the group consisting of: hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I or a pharmaceutically acceptable salt or solvate thereof, and a CETP inhibiting compound.

More particularly, an aspect of the invention that is of interest relates to a method of treating, delaying the onset, or preventing a condition selected from the group consisting of: hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I or a pharmaceutically acceptable salt or solvate thereof, and a CETP inhibiting compound selected from torcetrapib and anacetrapib.

Another aspect of the invention that is of interest relates to a pharmaceutical composition comprising (1) a compound of formula I as described above; (2) a compound selected from the list provide above in combination with a pharmaceutically acceptable carrier.

One pharmaceutical composition that is of interest is comprised of a compound of formula I as described herein, or a pharmaceutically acceptable salt or solvate thereof, in combination with a DPP-1V inhibitor selected from the group consisting of:

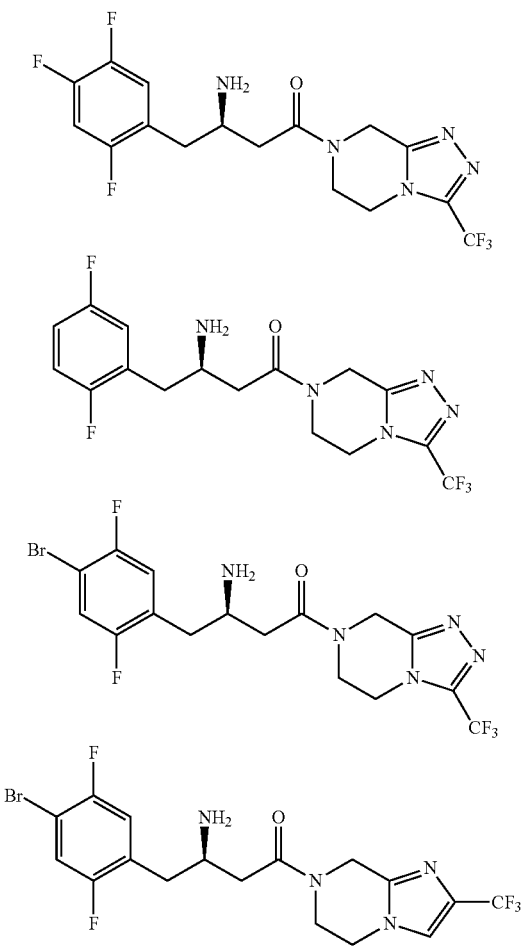

or a pharmaceutically acceptable salt or solvate thereof in combination with a pharmaceutically acceptable carrier.

Optical Isomers—Diastereomers—Geometric Isomers—Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixtures thereof are encompassed with the compounds of Formula I.

Salts and Solvates

Salts and solvates of compounds of formula I are included in the present invention. The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I are intended to include the pharmaceutically acceptable salts and solvates.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within the formulas described herein can be prepared without undue experimentation by conventional techniques well known to those skilled in the art or by processes analogous to those described in the Schemes and Examples herein using appropriate isotopically-enriched reagents and/or intermediates.

This invention relates to a method of inhibiting the activity of glucagon by antagonizing the glucagon receptor, thereby reducing the rate of gluconeogenesis and glycogenolysis, and the concentration of glucose in plasma.

The compounds of formula I can be used in the manufacture of a medicament for the prophylactic or therapeutic treatment of disease states in mammals associated with elevated levels of glucose, comprised of combining the compound of formula I with the carrier materials to provide the medicament.

Dose Ranges

The prophylactic or therapeutic dose of a compound of formula I will, of course, vary with the nature or severity of the condition to be treated, the particular compound selected and its route of administration. It will also vary according to the age, weight and response of the individual patient. In general, the daily dose range lies within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount", "anti-diabetic effective amount" and the other terms appearing throughout the application addressing the amount of the compound to be used refer to the dosage ranges provided, taking into account any necessary variation outside of these ranges, as determined by the skilled physician.

Representative dosages of compounds of formula I, as well as the pharmaceutically acceptable salts and solvates thereof, for adults range from about 0.1 mg to about 1.0 g per day, preferably about 1 mg to about 500 mg, in single or divided doses. Examples of suitable dosages include 0.1 mg, 1 mg, 2 mg, 5 mg, 10 mg, 20 mg, 40 mg, 50 mg, 75 mg, 100 mg, 150 mg, 200 mg, 250 mg, 500 mg, 1000 mg and similar such doses. Representative dosages of compounds used in combination with the compounds of formula I are known, or the determination thereof is within the level of skill in the art, taking into account the description provided herein.

When intravenous or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of formula I per kg of body weight per day.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human, with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like, in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets. Solid oral preparations are preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any acceptable pharmaceutical process. All such methods include the step of combining the active ingredient(s) with the carrier components. In general, the compositions are prepared by uniformly and intimately admixing the active ingredient(s) with a liquid or finely divided solid carrier component, and then, if necessary, manipulating the blend into the desired product form. For example, a tablet may be prepared by compression or molding. Compressed tablets may be prepared by compressing free-flowing powder or granules, containing the active(s) optionally mixed with one or more excipients, e.g., binders, lubricants, diluents, surfactants and dispersants. Molded tablets may be made by molding a mixture of the powdered compound moistened with an inert liquid. Desirably, each tablet may contain, for example, from about 0.1 mg to about 1.0 g of the active ingredient and each cachet or capsule contains from about 0.1 mg to about 500 mg of the active ingredient.

The following are examples of pharmaceutical dosage forms containing a compound of Formula I:

| Injectable Suspension (im.) | mg/mL | Tablet | Mg/tablet |
| --- | --- | --- | --- |
| Compound of Formula 1 | 10.0 | Compound of Formula 1 | 25.0 |
| Methylcellulose | 5.0 | Microcrystalline Cellulose | 415 |
| Tween 80 | 0.5 | Povidone | 14.0 |
| Benzyl alcohol | 9.0 | Pregelatinized Starch | 4.0 |
| Benzalkonium chloride | 1.0 | Magnesium Stearate | 2.5 |
| Water for injection | t.d. 1.0 mL | Total (approx.) | 460 mg |

| Capsule | mg/capsule | Aerosol | Per Canister |
| --- | --- | --- | --- |
| Compound of Formula 1 | 25.0 | Compound of Formula 1 | 250 mg |
| Lactose | 735 | Lecithin, NF Liq. Conc. | 1.2 mg |
| Mg Stearate | 1.5 | Trichloromethane, NF | 4.025 g |
| Total (approx.) | 761.5 mg | Dichlorodifluoromethane, NF | 12.15 g |

Combination Therapy

As previously described, the compounds of Formula I may be used in combination with other drugs that are used in the treatment/prevention/delaying the onset of type 2 diabetes mellitus, as well as other diseases and conditions described herein, for which compounds of Formula I are useful. Other drugs may be administered, by a route and in an amount commonly used, contemporaneously or sequentially with a compound of Formula I. When a compound of Formula I is used contemporaneously with one or more other drugs, a combination pharmaceutical composition containing such other drugs in addition to the compound of Formula I is preferred. Accordingly, the pharmaceutical compositions of the present invention include those that alternatively contain one or more other active ingredients, in addition to a compound of Formula I. Examples of other active ingredients that may be combined with a compound of Formula I, either administered separately or in the same pharmaceutical compositions, include, but are not limited to: (a) biguanides (e g., buformin, metformin, phenformin), (b) PPAR agonists (e.g., troglitazone, pioglitazone, rosiglitazone), (c) insulin, (d) somatostatin, (e) alpha-glucosidase inhibitors (e.g., voglibose, miglitol, acarbose), (f) DPP-IV inhibitors, such as sitagliptin, vildagliptin, saxagliptin, and the like, such as those disclosed in U.S. Pat. No. 6,699,871B1 granted on Mar. 2, 2004 (g) LXR modulators and (h) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide), and CB1 inhibitors, such as rimonabant and those compounds disclosed in WO03/077847A2 published on Sep. 25, 2003 and in WO05/000809 A1 published on Jan. 6, 2005.

An aspect of the invention that is particular interest relates to a pharmaceutical composition that is comprised of a compound of formula I, or a pharmaceutically acceptable salt thereof, and a member selected from the group consisting of: simvastatin, mevastatin, ezetimibe, atorvastatin, metformin, sibutramine, orlistat, Qnexa, topiramate, naltrexone, bupriopion, phentermine, losartan, hydrochlorothiazide, buformin, phenformin, troglitazone, pioglitazone, rosiglitazone, insulin, somatostatin, voglibose, miglitol, acarbose, sitagliptin, vildagliptin, saxagliptin, alogliptin, acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide, rimonabant and taranabant, in combination with a pharmaceutically acceptable carrier.

The weight ratio of the compound of the Formula I to the second active ingredient may be varied within wide limits and depends upon the effective dose of each active ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

When used in combination with other agents, the dosages noted above for the glucagon antagonist are provided along with the usual dose for the other medication. For example, when a DPP-IV inhibitor such as those disclosed in U.S. Pat. No. 6,699,871B1, is included, the DPP-IV inhibitor can be used in an amount ranging from about 1.0 mg to as high as about 1000 mg, preferably about 2.5 mg to about 250 mg, and in particular, about 50 mg or about 100 mg administered in single daily doses or in divided doses as appropriate. Similarly, when the glucagon receptor antagonist is used in combination with a CB1 antagonist/inverse agonist, the CB1 antagonist/inverse agonist can be used in an amount ranging from as low as about 0.1 mg to as high as about 1000 mg, more particularly, in an amount ranging from about 1.0 mg to about 100 mg, and even more particularly, in an amount from about 1.0 mg to about 10 mg, administered in single daily doses or in divided doses as appropriate. Examples of doses of CB1 antagonist/inverse agonist include 1 mg, 2 mg, 3 mg, 4 mg, 5 mg, 6 mg, 7 mg, 8 mg, 9 mg, 10 mg and 20 mg.

Methods of Synthesis:

Compounds of the present invention can be prepared according to the Schemes provided below as well as the procedures provided in the Examples. The substituents are the same as in the above Formulas except where defined otherwise or otherwise apparent to the ordinary skilled artisan.

The novel compounds of the present invention can be readily synthesized using techniques known to those skilled in the art, such as those described, for example, in *Advanced Organic Chemistry*, March, 5$^{th}$ Ed., John Wiley and Sons, New York, N.Y., 2001; *Advanced Organic Chemistry*, Carey and Sundberg, Vol. A and B, 3$^{rd}$ Ed., Plenum Press, Inc., New York, N.Y., 1990; *Protective groups in Organic Synthesis*, Green and Wuts, 2$^{nd}$ Ed., John Wiley and Sons, New York, N.Y., 1991; *Comprehensive Organic Transformations*, Larock, VCH Publishers, Inc., New York, N.Y., 1988; *Handbook of Heterocyclic Chemistry*, Katritzky and Pozharskii, 2$^{nd}$ Ed., Pergamon, New York, N.Y., 2000 and references cited therein. The starting materials for the present compounds may be prepared using standard synthetic transformations of chemical precursors that are readily available from commercial sources, including Aldrich Chemical Co. (Milwaukee, Wis.); Sigma Chemical Co. (St. Louis, Mo.); Lancaster Synthesis (Windham, N.H.); Ryan Scientific (Columbia, S. C.); Maybridge (Cornwall, UK); Matrix Scientific (Columbia, S. C.); Acros, (Pittsburgh, Pa.); BiolBlocks, Inc. (San Diego, Calif.); and Trans World Chemicals (Rockville, Md.).

The procedures described herein for synthesizing the compounds may include one or more steps of protecting group manipulations and of purification, such as, re-crystallization, distillation, column chromatography, flash chromatography, thin-layer chromatography (TLC), and high-pressure chromatography (HPLC). The products can be characterized using various techniques well known in the chemical arts, including proton and carbon-13 nuclear magnetic resonance ($^1$H and $^{13}$C NMR), infrared and ultraviolet spectroscopy (IR and UV), X-ray crystallography, elemental analysis and HPLC and mass spectrometry (HPLC-MS). Methods of protecting group manipulation, purification, structure identification and quantification are well known to one skilled in the art of chemical synthesis.

Appropriate solvents are those which will at least partially dissolve one or all of the reactants and will not adversely interact with either the reactants or the product. Suitable solvents are aromatic hydrocarbons (e.g. toluene, xylenes), halogenated solvents (e.g. methylene chloride, chloroform, carbon tetrachloride, chlorobenzenes), ethers (e.g. diethyl ether, diisopropyl ether, tert-butyl methyl ether, diglyme, tetrahydrofuran, dioxane, anisole), nitriles (e.g. acetonitrile, propionitrile), ketones (e.g. 2-butanone, diethyl ketone, tert-butyl methyl ketone), alcohols (e.g. methanol, ethanol, n-propanol, iso-propanol, n-butanol, t-butanol), N,N-dimethyl formamide (DMF), dimethylsulfoxide (DMSO) and water. Mixtures of two or more solvents can also be used. Suitable bases are, generally, alkali metal hydroxides, alkaline earth metal hydroxides such as lithium hydroxide, sodium hydroxide, potassium hydroxide, barium hydroxide, and calcium hydroxide; alkali metal hydrides and alkaline earth metal hydrides such as lithium hydride, sodium hydride, potassium hydride and calcium hydride; alkali metal amides such as lithium amide, sodium amide and potassium amide; alkali metal carbonates and alkaline earth metal carbonates such as lithium carbonate, sodium carbonate, cesium carbonate, sodium hydrogen carbonate, and cesium hydrogen carbonate; alkali metal alkoxides and alkaline earth metal alkoxides such as sodium methoxide, sodium ethoxide, potassium tert-butoxide and magnesium ethoxide; alkali metal alkyls such as methyllithium, n-butyllithium, sec-butyllithium, t-bultyllithium, phenyllithium, alkyl magnesium halides, organic bases such as trimethylamine, triethylamine, triisopropylamine, N,N-diisopropylethyl amine, piperidine, N-methyl piperidine, morpholine, N-methyl morpholine, pyridine, collidines, lutidines, and 4-dimethylaminopyridine; and bicyclic amines such as DBU and DABCO.

It is understood that the functional groups present in compounds described in the Schemes below can be further manipulated, when appropriate, using the standard functional group transformation techniques available to those skilled in the art, to provide desired compounds described in this invention.

Throughout the synthesis schemes, abbreviations are used with the following meanings unless otherwise indicated:

| | |
|---|---|
| AIBN = azobisisobutyronitrile | aq = aqueous |
| BINAP = 2,2'-bis(diphenylphosphino)-1,1'-binaphthalene | Bn = benzyl |
| BOC, Boc = t-butyloxycarbonyl | BOP = benzotriazol-1-yloxy-tris(dimethylamino)-phosphonium hexafluorophosphate |
| Bu = butyl, t-Bu = t-butyl | BuLi, n-BuLi = n-butyllithium |
| CBZ, Cbz = Benzyloxycarbonyl | CDI = 1,1'-carbonyldiimidazole |
| (S)-DAIPEN = (S)-1,1-di(4-anisyl)-2-isopropyl-1,2-ethylenediamine = (S)-1,1-bis(4-methoxyphenyl)-3-methylbutane-1,2-diamine | dba = dibenzylideneacetone = trans, trans-1,5-diphenyl-1,4-pentadien-3-one |
| DCM = dichloromethane | 2,4-diClPh = 2,4-dichlorophenyl |
| DIPEA = DIEA = diisopropylethylamine | DMAP = 4-Dimethylaminopyridine |
| DMF = N,N-dimethylformamide | DMS = dimethyl sulfide |
| DMSO = dimethyl sulfoxide | dppf = 1,1'-bis(diphenylphosphino) ferrocene |
| EDC = 1-ethyl-3-(3-dimethylaminopropyl)-carbodiimide | eq. = equivalent(s) |
| Et = ethyl | EtOAc = ethyl acetate |
| EtOH = ethanol | g = gram(s) |
| HATU = O-(7-azabenzotriazol-1-yl)-N,N,N',N'-tetramethyluronium hexafluorophosphate | HOBT, HOBt = 1-hydroxybenzotriazole |
| HPLC = High pressure liquid chromatography | IPA = isopropanol = 2-propanol |
| iPr = isopropyl = 2-propyl | KHMDS = potassium bis(trimethylsilyl)amide |
| KOtBu = potassium tert-butoxide | LC/MS = liquid chromatography-mass spectrometry |
| LDA = lithium diisopropylamide | LHMDS = lithium bis(trimethylsilyl)amide |
| M = molar | mCPBA = 3-chloroperoxybenzoic acid |
| Me = methyl | MeCN, CH$_3$CN = acetonitrile |
| MeOH = methanol | mg = milligram(s) |
| mL = milliliter(s) | mmol = millimole(s) |
| MTBE = TBME = methyl t-butyl ether | N = normal |
| NaOtBu = sodium tert-butoxide | NBS = N-bromosuccinimide |
| NCS = N-chlorosuccinimide | NMP = 1-methyl-2-pyrrolidinone |
| n-Pr = n-propyl | PCC = pyridinium chlorochromate |
| Pd/C = palladium on activated carbon | Ph = phenyl |
| PyBOP = Benzotriazol-1-yloxytripyrrolidinophosphonium hexafluorophosphate | RT, rt = room temperature |

| | |
|---|---|
| TBAF = tetrabutylammonium fluoride | Tf = triflate = trifluoromethanesulfonate |
| TFA = Trifluoroacetic acid | THF = tetrahydrofuran |
| TMS = trimethylsilyl | Tr = trityl = triphenylmethyl |
| (S)-xyl-SEGPHOS = (S)-5,5'-Bis[di(3,5-xylyl)phosphino]-4,4'-bi-1,3-benzodioxole | |

Compounds of the present invention may be prepared according to the methodology outlined in the following general synthetic schemes.

Multiple embodiments of the present invention are summarized in Scheme 1 which depicts the preparation of compounds Ia and Ib. Treating t-butyl esters 1 or 2 with an acid such as acetic acid or trifluoroacetic acid (TFA) can afford compound Ia. In the case of ester 2, the Boc protecting group is removed in this process providing compound Ia in which $R^4$=H. In a closely related second embodiment of the invention, treating t-butyl ester 3 under acidic conditions affords compound Ib. An additional embodiment of the invention involves formation of compound Ia from indole 4, the preparation of which is detailed in PCT Patent Publication WO 2008/042223 A1 published on 10 Apr. 2008. Treatment of 4 with ozone gas in methanol solvent at −78° C. followed by the addition of dimethylsulfide can afford a mixture of ketones 5a and 5b, which can then be converted completely to 5b by heating the mixture with aqueous acid, such as hydrochloric acid, in a solvent such as THF. Intermediate 5b can then be nitrosated with sodium nitrite and hydrochloric acid, and subsequently reduced with tin (II) chloride, to afford compound Ia in which $R^4$=H following the procedure described in *Synthetic Communications*, Sasakura, K., et. al., 1988, 259-264.

Scheme 1

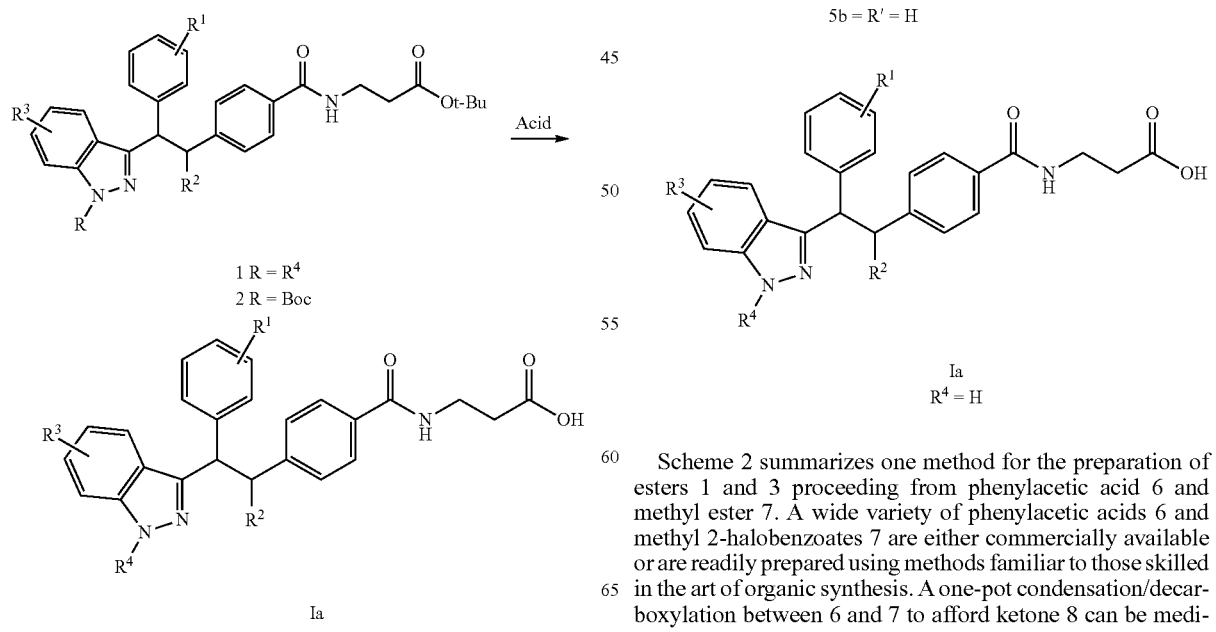

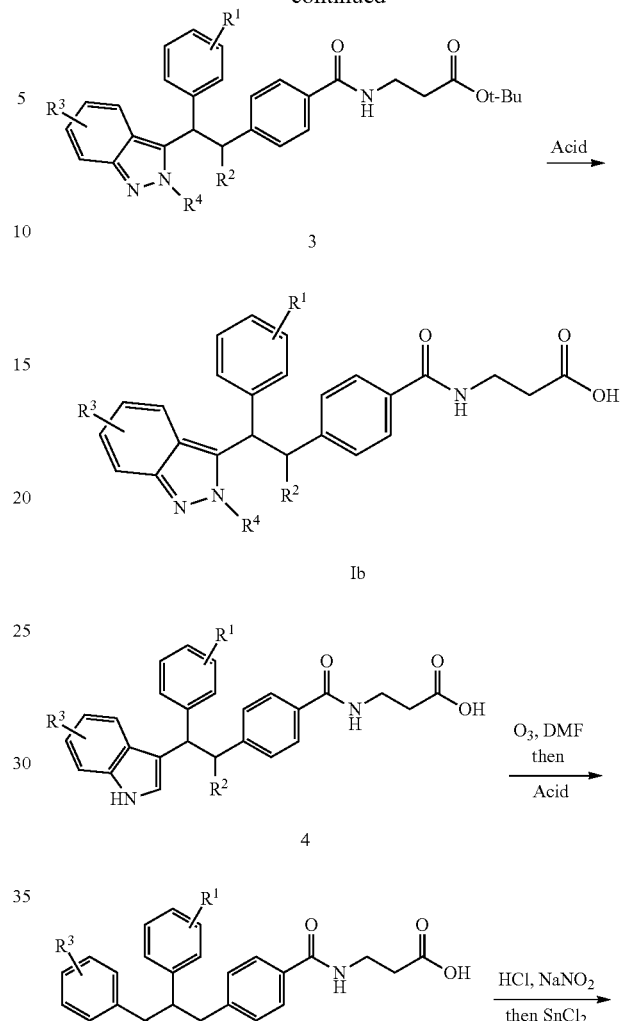

Scheme 2 summarizes one method for the preparation of esters 1 and 3 proceeding from phenylacetic acid 6 and methyl ester 7. A wide variety of phenylacetic acids 6 and methyl 2-halobenzoates 7 are either commercially available or are readily prepared using methods familiar to those skilled in the art of organic synthesis. A one-pot condensation/decarboxylation between 6 and 7 to afford ketone 8 can be mediated by a base such as NaHMDS in a solvent such as THF at low temperatures such as −78° C. Enolization of ketone 8 with a base such as sodium hydride in a solvent such as DMF and subsequent addition of bromide 9 (also readily prepared using methods familiar to those skilled in the art of organic synthesis) can then provide intermediate 10. Deprotection of the t-butyl ester of 10 can be accomplished using the acidic conditions described for the conversion of 1 to Ia (Scheme 1). The carboxylic acid intealuediate 11 can be coupled with t-butyl (3-alanine ester using O-(7-azabenzotriazol-1-yl)-N,N,N',N'-tetramethyluronium hexafluorophosphate (HATU) and a base, generally N,N-diisopropylethylamine (DIPEA), in a solvent such as N,N-dimethylformamide (DMF), 1-methyl-2-pyrrolidinone (NMP), or dichloromethane (DCM) at ambient temperature to yield amide 12. Alternatively, the conversion of 11 to 12 may be carried out with EDC, HOBt, and a base such as DIPEA in similar solvents as those used with HATU and DIPEA. Many additional peptide coupling conditions are known and may also be used. The preparation of esters 1 and 3 can be completed by condensation of intermediate 12 with an appropriate hydrazine 13 in a solvent such as pyridine or DMSO at temperatures between room temperature and 100° C. This condensation generally favors formation of 3, except in the case of hydrazine and methylhydrazine ($R^4$=H or Me), when 1 is usually the predominant product. A wide range of substituents may be introduced at the $R^1$, $R^2$, $R^3$, and $R^4$ positions on esters 1 and 3 due to the functional group tolerance of the reactions employed in their preparation and the wide variety of starting acids 6, esters 7, bromides 9, and hydrazines 13 which are either commercially available or readily prepared by methods known to those skilled in the art of organic synthesis.

Scheme 2

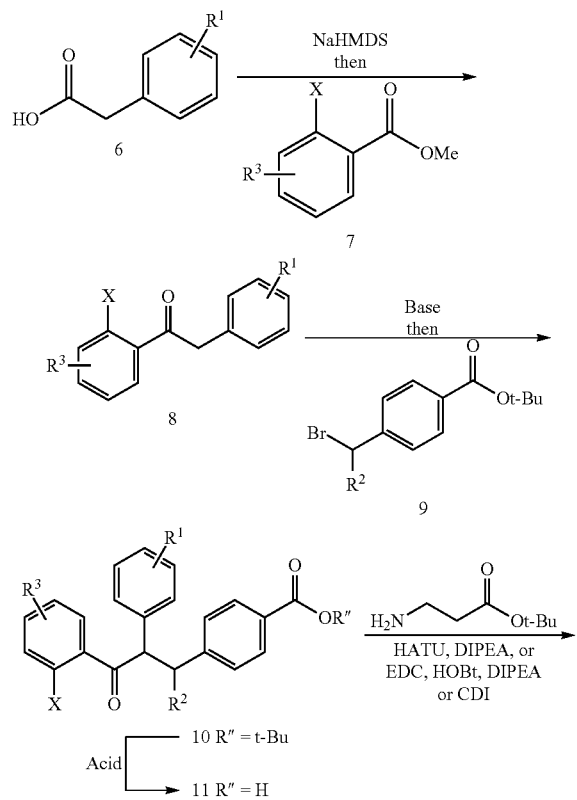

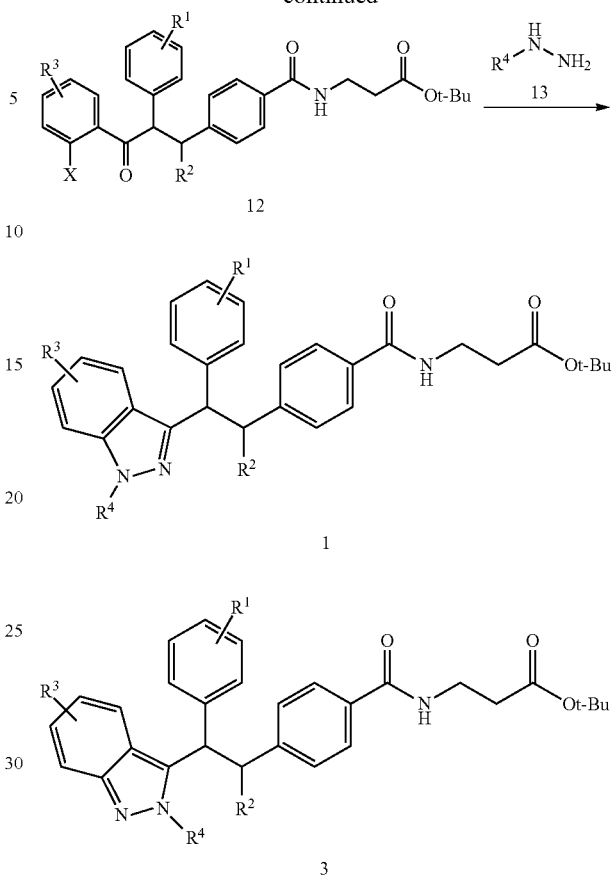

X = F, Cl

While the $R^3$ and $R^4$ substituents are usually introduced on ester 7 and hydrazine 13, respectively, it is also possible to alter these substituents on advanced intermediates as shown in Scheme 3. For instance, the unsubstituted indazole 1a (prepared as described in Scheme 2) can be converted to a mixture of 1- and 2-substituted indazoles 1b and 3a in the presence of an alkylating agent and a base such as cesium carbonate in a polar aprotic solvent such as NMP. In a different example, the unsubstituted indazole 1c can be protected with a Boc protecting group to afford intermediate 2a using di-t-butyl dicarbonate and a base such as cesium carbonate in a polar aprotic solvent such as DMF. The bromide substituent of 2a can then be functionalized utilizing a wide variety of metal-mediated transformations that will be obvious to those skilled in the art of organic synthesis. For instance, 2a can be converted to 2b under Suzuki coupling conditions with an aryl or heteroaryl boronic acid, palladium catalyst such as $(PPh_3)_4Pd$, base such as sodium carbonate, in a mixed solvent system such as THF and water, at temperatures between 70° C. and 200° C. Under these conditions, some amount of 2a may also be converted to 2c, in which the bromide substituent has been replaced with a hydrogen atom. Alternatively, the bromide substituent of compound 2a can be converted to nitrile 2d in the presence of a palladium catalyst such as $Pd(PPh_3)_4$ and a cyanide source such as $Zn(CN)_2$ in a polar aprotic solvent such as DMF at a temperature of 120° C. based on the chemistry described by Kubota and Rice, *Tetrahedron Letters*, 1998, 39, 2907-2910.

Scheme 3
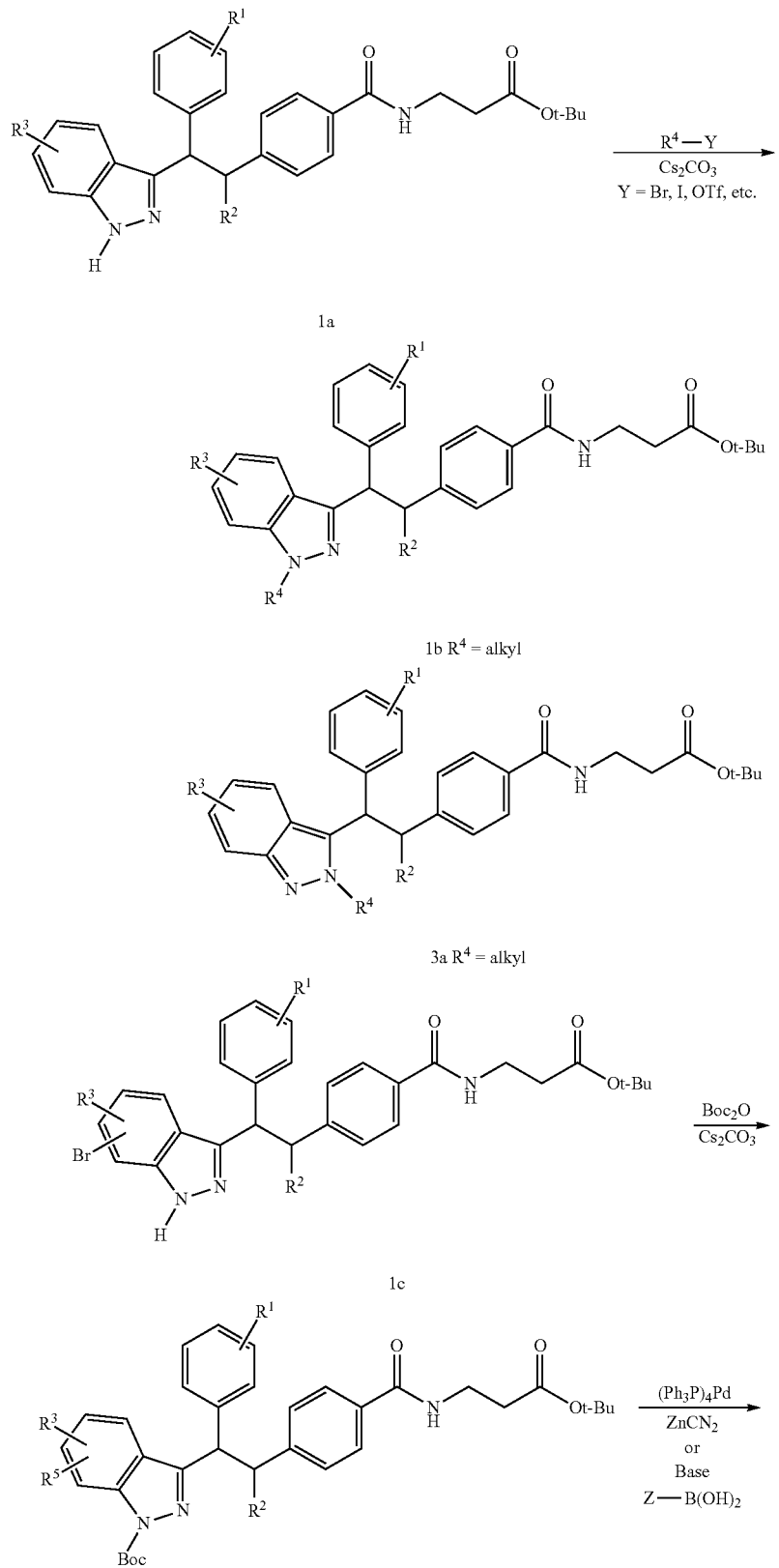

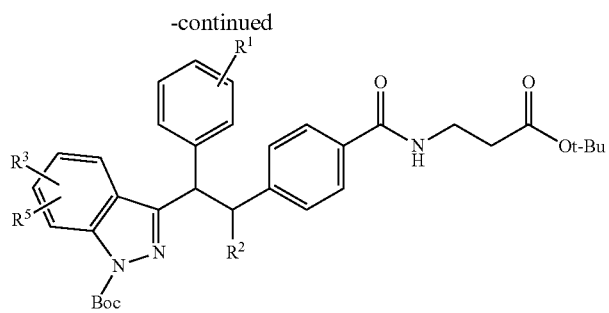

2b R⁵ = Z= Aryl or Heteroaryl
2c R⁵ = H
2d R⁵ = CN

While a wide variety of intermediates 10 may be prepared using readily available substrates as described in Scheme 2, the preparation of 10a entailed the use of a silicon protecting group as depicted in Scheme 4. Commercially available arene 14 can be deprotonated by treatment with a strong base such as LDA in an ethereal solvent such as THF at sub-ambient temperature then silylated with TMSCl to afford silyl arene 15. Deprotonation of 15 with a strong base such as lithium 2,2,6,6-tetramethylpiperidide at low temperature followed by addition of solid carbon dioxide can afford carboxylic acid 16. Conversion to methyl ester 17 can be achieved by addition of an acid such as sulfuric acid to a methanol solution of 16. Methyl ester 17 can then be converted to intermediate 10a using the same chemistry described in Scheme 2 for the conversion of 7 to 10. The trimethylsilyl group was found to be removed under the conditions employed for the condensation of ketone 18 with bromide 9.

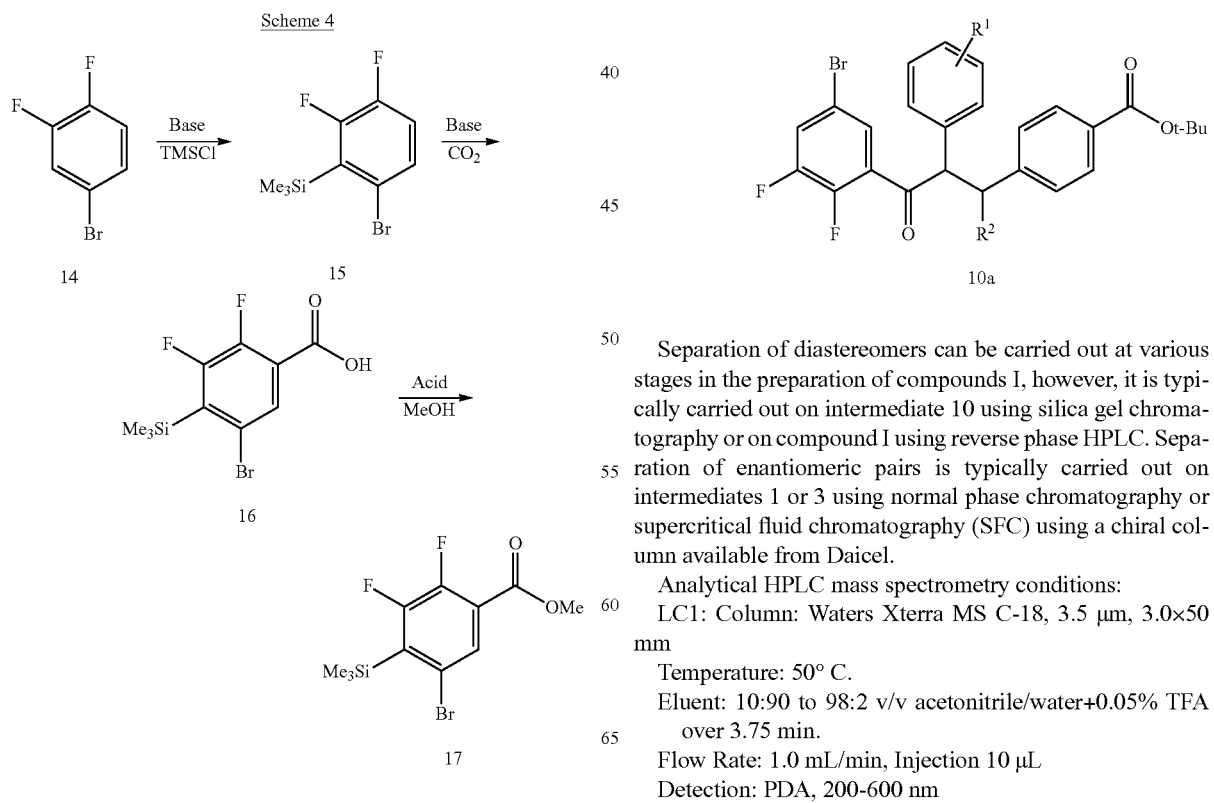

Scheme 4

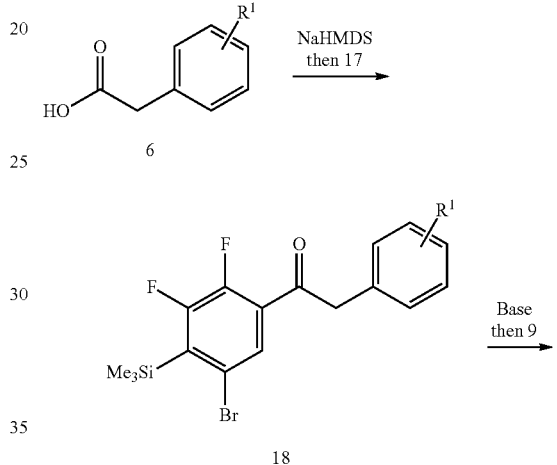

Separation of diastereomers can be carried out at various stages in the preparation of compounds I, however, it is typically carried out on intermediate 10 using silica gel chromatography or on compound I using reverse phase HPLC. Separation of enantiomeric pairs is typically carried out on intermediates 1 or 3 using normal phase chromatography or supercritical fluid chromatography (SFC) using a chiral column available from Daicel.

Analytical HPLC mass spectrometry conditions:
LC1: Column: Waters Xterra MS C-18, 3.5 µm, 3.0×50 mm
Temperature: 50° C.
Eluent: 10:90 to 98:2 v/v acetonitrile/water+0.05% TFA over 3.75 min.
Flow Rate: 1.0 mL/min, Injection 10 µL
Detection: PDA, 200-600 nm MS: mass range 150-750 amu; positive ion electrospray ionization LC2: Column: Waters Xterra IS C-18, 3.5 μm, 2.1×20 mm Temperature: 50° C.

Eluent: 5:95 to 95:5 v/v acetonitrile/water+0.05% TFA over 1.75 min.

Flow Rate: 1.5 mL/min, Injection 5 μL

Detection: PDA, 200-600 nm

MS: mass range 150-750 amu; positive ion electrospray ionization

LC3: Column: Waters Xterra IS C-18, 3.5 μm, 3.0×50 mm

Temperature: 50° C.

Eluent: 10:90 to 98:2 v/v acetonitrile/water+0.05% TFA over 1.25 min.

Flow Rate: 1.5 mL/min, Injection 5 μL,

Detection: PDA, 200-600 nm

MS: mass range 150-750 amu; positive and negative ion electrospray ionization

Preparative reverse phase HPLC conditions:

Column: Xterra MS, 5 μm, 30×100 mm

Flow Rate: 40.0 mL/min

Eluent: acetonitrile/water+0.1% TFA

Gradient: 10:90 to 100:0 v/v acetonitrile/water+0.1% TFA over 20.0 min.

Temperature: ambient

Detection: PDA, 254 nm

Preparative thin layer chromatography (PTLC) was performed on 20×20 cm plates (500 μm thick silica gel) using hexanes/ethyl acetate or (DCM/MTBE)/hexanes or DCM/hexanes as eluent. Silica gel chromatography was performed on a Biotage Horizon flash chromatography system using a hexanes/ethyl acetate, (DCM/MTBE)/hexanes or DCM/hexanes eluent.

The following examples are provided so that the invention might be more fully understood. They should not be construed as limiting the invention in any way.

Intermediate 1

Tert-Butyl N-[4-(1-{1-(4-Chlorophenyl)-2-[2-Fluoro-5-(Trifluoromethyl)Phenyl]-2-Oxoethyl}Butyl)Benzoyl]-β-Alaninate

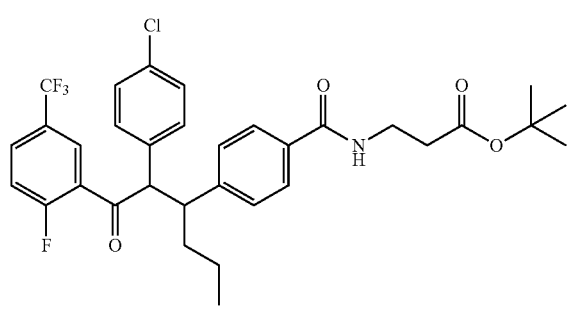

Step A. 2-(4-Chlorophenyl)-1-[2-fluoro-5-(trifluoromethyl)phenyl]ethanone

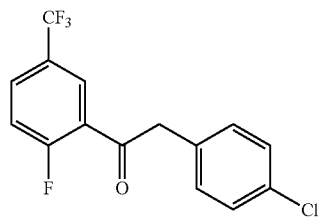

A solution of 4-chlorophenylacetic acid (2.074 g, 12.15 mmol) in THF (16 mL) was added drop wise over three minutes to NaHMDS (1.0 M in THF, 33 mL, 33 mmol) at −78° C., then the solution was stirred for five minutes. A solution of methyl 2-fluoro-5-(trifluoromethyl)benzoate (1.93 ml, 12.2 mmol) in THF (16 mL) was added in portions over five minutes, then the solution was stirred at −78° C. for five hours. The solution was diluted with 2 N HCl (aq, 300 mL) then extracted twice with EtOAc. The combined organic layers were dried over $Na_2SO_4$, filtered, then concentrated. The residue was purified by silica gel chromatography eluting with 0-50% DCM/hexanes to afford the title compound as a yellow liquid. $^1$H NMR (500 MHz, $CDCl_3$): δ 8.15 (dd, J=6.5, 2.3 Hz, 1H); 7.81-7.77 (m, 1H); 7.31-7.24 (m, 3H); 7.17 (d, J=8.2 Hz, 2H); 4.27 (d, J=2.7 Hz, 2H).

Step B. tert-Butyl 4-(1-{1-(4-chlorophenyl)-2-[2-fluoro-5-(trifluoromethyl)phenyl]-2-oxoethyl}butyl)benzoate

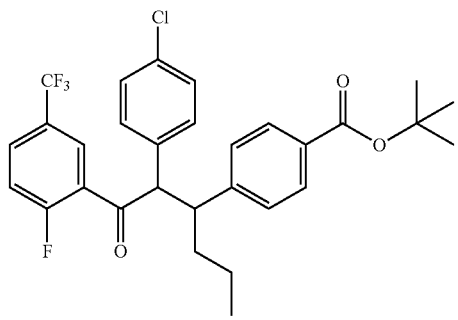

To a slurry of NaH (60 wt % in mineral oil, 93 mg, 2.3 mmol) in DMF (2 mL) at 0° C. was added the product of Step A (250 mg, 0.789 mmol), then the mixture was stirred for one hour. A solution of methyl 4-(1-bromobutyl)benzoate (0.30 mL, 1.18 mmol) in DMF (2 mL) was added, then the mixture was allowed to warm to RT over five hours. The mixture was diluted with saturated $NH_4Cl$ (aq) then extracted twice with EtOAc. The combined organic layers were dried over $Na_2SO_4$, filtered, then concentrated. The residue was purified, and diastereomers were separated, by silica gel chromatography eluting with 0-60% DCM/hexanes to afford racemic mixtures of the two diastereomeric title compounds.

Faster-eluting diastereomer: ¹H NMR (500 MHz, CDCl₃): δ 8.07 (d, J=6.5 Hz, 1H); 7.78-7.72 (m, 3H); 7.04 (t, J=7.7 Hz, 4H); 6.97 (d, J=8.3 Hz, 2H); 4.72 (d, J=10.8 Hz, 1H); 3.66-3.57 (m, 1H); 1.84-1.64 (m, 2H); 1.56 (s, 9H); 1.17-0.99 (m, 2H); 0.84-0.78 (m, 3H).

Slower-eluting diastereomer: ¹H NMR (500 MHz, CDCl₃): δ 7.84 (d, J=8.0 Hz, 2H); 7.62-7.58 (m, 1H); 7.51 (d, J=6.5 Hz, 1H); 7.39 (d, J 8.2 Hz, 2H; 7.34 (d, J=8.4 Hz, 2H); 7.29 (d, J 8.2 Hz, 2H); 7.11 (t, J=9.5 Hz, 1H); 4.78 (d, J=11.0 Hz, 1H); 3.52-3.43 (m, 1H); 1.56 (s, 9H); 1.35-1.24 (m, 2H); 1.05-0.84 (m, 2H); 0.72-0.66 (m, 3H).

Step C. text-Butyl N-[4-(1-{1-(4-chlorophenyl)-2-[2-fluoro-5-(trifluoromethyl)phenyl]-2-oxoethyl}butyl)benzoyl]-β-alaninate

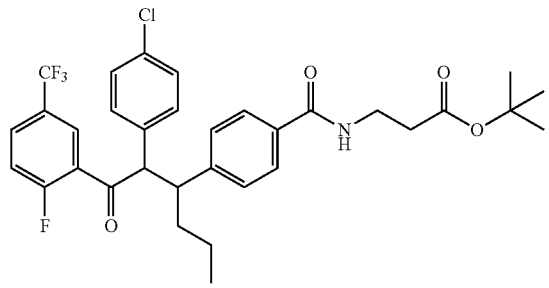

To a solution of the faster-eluting diastereomer of the product from Step B (482 mg, 0.878 mmol) and anisole (0.01 mL, 0.092 mmol) in DCM (5 mL) was added TFA (5 mL, 64.9 mmol). After one hour, the solution was concentrated to afford the carboxylic acid product. After being dried on high vacuum, the material was used directly in the next step without further purification.

To a solution of the product of the previous step in NMP (8 mL) was added DIPEA (0.770 mL, 4.4 mmol) then HATU (434 mg, 1.14 mmol). After the mixture was stirred for one hour, tert-butyl-β-alaninate hydrochloride (239 mg, 1.32 mmol) was added, then the mixture was stirred for an additional hour at RT. The mixture was diluted with saturated NaCl (aq) then extracted twice with EtOAc. The combined organic layers were dried over Na₂SO₄, filtered, then concentrated. The residue was purified by silica gel chromatography eluting with 0-100% EtOAc/hexanes to afford the racemic title compound as a colorless syrup. ¹H NMR (500 MHz, CDCl₃): δ 8.07 (dd, J=6.5, 2.3 Hz, 1H); 7.77-7.71 (m, 1H); 7.54 (d, J=8.0 Hz, 2H); 7.05 (d, J=8.2 Hz, 2H); 7.01 (d, J=8.0 Hz, 2H); 6.95 (d, J=8.3 Hz, 2H); 6.78-6.73 (m, 1H); 4.70 (d, J=10.80 Hz, 1H); 3.72-3.57 (m, 3H); 2.60-2.50 (m, 2H); 1.83-1.65 (m, 2H); 1.54-1.38 (m, 9H); 1.18-0.98 (m, 2H); 0.82 (t, J=7.3 Hz, 3H); LC2 1.57 min. (M-tBu+H)⁺ 564.

The racemic other diastereomer of the title compound was obtained by applying the same procedure to the slower-eluting diastereomer of the product of Step B. LC2 1.58 min. (M-tBu+H)⁺ 564.

EXAMPLE 1

N-(4-{1-(5-Chloro-7-Methyl-1H-Indazol-3-Yl)(4-Chlorophenyl)Methyl]Butyl}Benzoyl)-β-Alanine

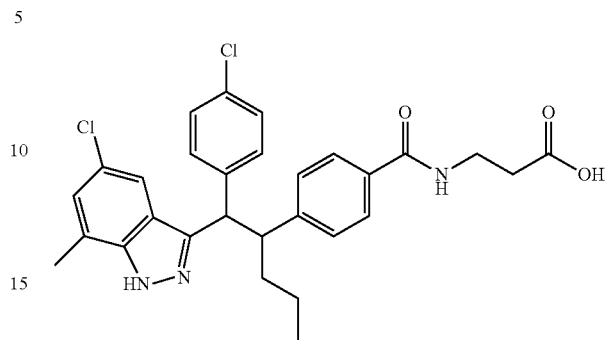

Step A. tert-Butyl N-(4-{1-[1-(4-chlorophenyl)-2-(2,5-dichloro-3-methylphenyl)-2-oxoethyl]butyl}benzoyl)-β-alaninate

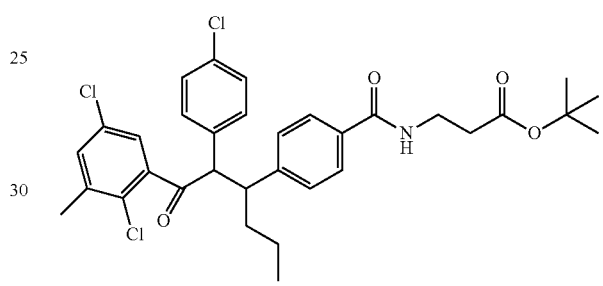

Using the procedure from INTERMEDIATE 1, methyl 2,5-dichloro-3-methylbenzoate was converted to the two diastereomers of the title compound.

Major diastereomer: ¹H NMR (500 MHz, CDCl₃): δ7.51 (d, J=8.2 Hz, 2H); 7.24 (d, J=2.3 Hz, 1H); 7.03 (d, J=8.3 Hz, 2H); 7.01 (d, J=8.4 Hz, 2H); 7.01 (d, J=8.4 Hz, 2H); 6.90-6.83 (m, 3H); 6.75 (t, J=6.0 Hz, 1H); 4.53 (d, J=11.0 Hz, 1H); 3.64-3.55 (m, 3H); 2.51 (t, J=6.0 Hz, 2H); 2.36 (s, 3H); 2.01-1.93 (m, 1H); 1.77-1.66 (m, 1H); 1.44 (s, 9H); 1.18-1.01 (m, 2H); 0.85 (t, J=7.3 Hz, 3H).

Minor Diastereomer: ¹H NMR (500 MHz, CDCl₃): δ 7.67 (d, J=8.2 Hz, 2H); 7.38-7.30 (m, 6H); 7.11 (d, J=2.3 Hz, 1H); 6.85 (t, J=5.7 Hz, 1H); 6.27 (d, J=2.5 Hz, 1H); 4.50 (d, J=11.0 Hz, 1H); 3.68 (q, J=5.6 Hz, 2H); 3.43 (td, J=11.2, 3.0 Hz, 1H); 2.55 (t, J=5.8 Hz, 2H); 2.23 (s, 3H); 1.47 (s, 9H); 1.46-1.35 (m, 1H); 1.29-1.01 (m, 1H); 1.00-0.86 (m, 2H); 0.67 (t, J=7.3 Hz, 3H).

Step B. tert-Butyl N-(4-{1-[(5-chloro-7-methyl-1H-indazol-3-yl)(4-chlorophenyl)methyl]butyl}benzoyl)-β-alaninate

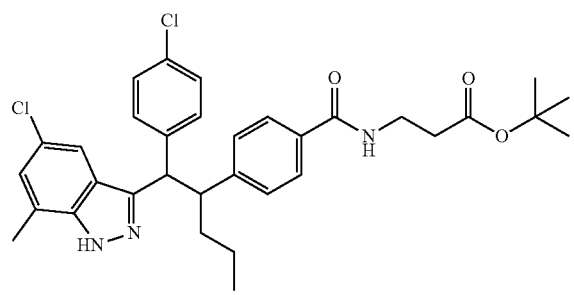

To a solution of the major diastereomer of the product of Step A (271 mg, 0.439 mmol) in DMSO (25 mL) was added hydrazine hydrate (60 wt %, 0.90 mL, 11 mmol). The mixture was stirred at 100° C. for two days in a sealed tube. The mixture was diluted with saturated NaCl (aq) then extracted twice with ethyl acetate. The combined organic layers were then washed with 2 N HCl (aq), saturated NaHCO$_3$ (aq), and saturated NaCl (aq). The organic layer was dried over sodium sulfate, filtered, then concentrated. The resulting residue was purified by silica gel chromatography eluting with 0-50% EtOAc/hexanes to afford the major diastereomer of the title compound as a solid. This diastereomer was resolved to provide enantiopure material by supercritical fluid chromatography on a ChiralPak OJ-H column (2 cm×25 cm) eluting with 50 mL/min of 20% (MeOH+0.1% Et$_2$NH) and 80% CO$_2$ at 35° C. and 100 bar. LC1 2.58 min. (M-tBu+H)$^+$ 538.

The minor diastereomer of the title compound was obtained by applying the same procedure to the minor diastereomer of the product of Step A. This diastereomer was resolved to provide enantiopure material by supercritical fluid chromatography on a ChiralPak AD-H column (3 cm×25 cm) eluting with 50 mL/min of 40% (IPA+0.1% Et$_2$NH) and 60% CO$_2$ at 35° C. and 100 bar. LC1 2.63 min. (M-tBu+H)$^+$ 538.

Step C. N-(4-{1-[(5-Chloro-7-methyl-1H-indazol-3-yl)(4-chlorophenyl)methyl]butyl}benzoyl)-β-alanine

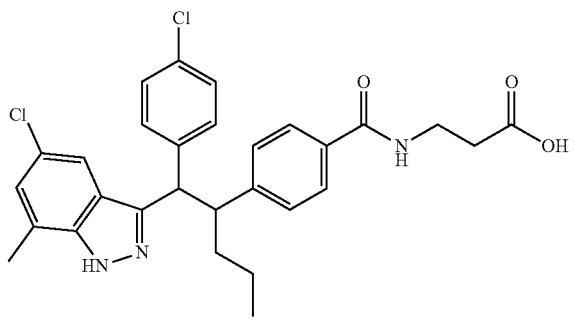

To a solution of the faster-eluting enantiomer of the minor diastereomer of the product from Step B (18 mg, 0.030 mmol) in DCM (2 mL) was added TFA (2 mL, 26 mmol), and the solution was stirred for 30 minutes at RT. The solution was concentrated, then the residue was purified by reverse phase HPLC eluting with acetonitrile/water+0.1% TFA. Following lyophilization, this afforded the enantiopure title compound as a white solid. This was the most potent glucagon antagonist of the four stereoisomeric compounds. $^1$H NMR (500 MHz, CD$_3$OD): δ 7.60 (d, J=8.2 Hz, 2H); 7.55 (s, 1H); 7.51 (d, J=8.3 Hz, 2H); 7.35 (d, J=8.3 Hz, 2H); 7.31 (d, 3=8.5 Hz, 2H); 6.95 (s, 1H); 4.69 (d, J=11.7 Hz, 1H); 3.80 (td, J=11.5, 3.4 Hz, 1H); 3.52 (t, J=7.0 Hz, 2H); 2.55 (t, J=7.0 Hz, 2H); 2.35 (s, 3H); 1.61-1.46 (m, 2H); 1.04-0.98 (m, 2H); 0.73 (t, J=7.3 Hz, 3H); LC2 1.39 min. (M+H)$^+$ 538.

The other stereoisomers of the title compound were prepared as enantiopure compounds from the enantiopure tert-butyl ester starting materials using the same procedure. Characterization data for one of the diastereomeric products are as follows. $^1$H NMR (500 MHz, CD$_3$OD): δ 7.70 (s, 1H); 7.61 (d, J=8.0 Hz, 2H); 7.31 (d, J=8.0 Hz, 2H); 7.24 (d, J=8.3 Hz, 2H); 7.12 (s, 1H); 6.99 (d, J=8.3 Hz, 2H); 4.66 (d, J=11.6 Hz, 1H); 3.86-3.80 (m, 1H); 3.58 (t, J=7.0 Hz, 2H); 2.60 (t, J=7.0 Hz, 2H); 2.53 (s, 3H); 1.62 (q, J=7.5 Hz, 2H); 1.04 (td, J=15.1, 7.5 Hz, 2H); 0.71 (t, J=7.3 Hz, 3H); LC2 1.39 min. (M+H)$^+$ 538.

EXAMPLE 2

N-(4-{1-[[7-Chloro-1-Methyl-5-(Trifluoromethyl)-1H-Indazol-3-Yl](4-Chlorophenyl)Methyl]Butyl}Benzoyl)-β-Alanine

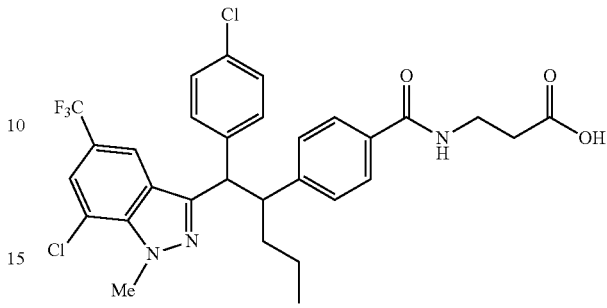

Step A. tert-Butyl N-(4-{1-[2-[3-chloro-2-fluoro-5-(trifluoromethyl)phenyl]-1-(4-chlorophenyl)-2-oxoethyl]butyl}benzoyl)-β-alaninate

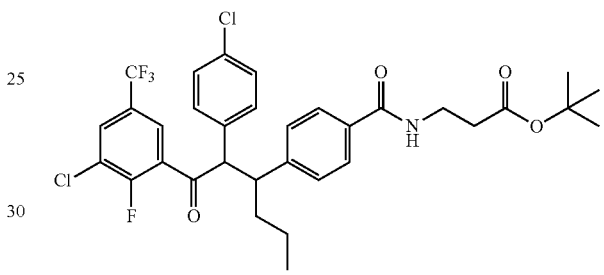

Using the procedure from INTERMEDIATE 1, methyl 3-chloro-2-fluoro-5-(trifluoromethyl)benzoate was converted to the two diastereomers of the title compound. Major diastereomer: LC2 1.62 min. (M-tBu+H)$^+$ 598. Minor diastereomer: LC2 1.61 min. (M-tBu+H)$^+$ 598.

Step B. tert-Butyl N-(4-{1-[[7-chloro-1-methyl-5-(trifluoromethyl)-1H-indazol-3-yl](4-chlorophenyl)methyl]butyl}benzoyl)-β-alaninate

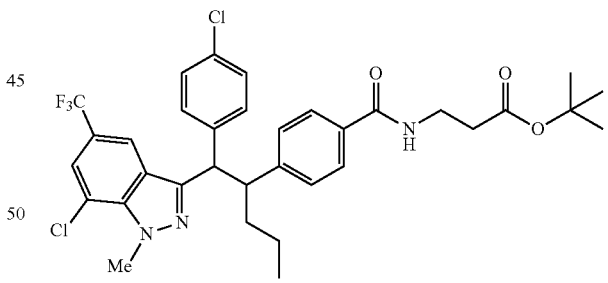

To a solution of the major diastereomer of the product of Step A (40 mg, 0.061 mmol) in pyridine (3 mL) was added methylhydrazine (0.016 mL, 0.306 mmol). The mixture was stirred at 80° C. for two hours in a sealed tube then stirred at RT overnight. The mixture was diluted with EtOAc, then washed with 1 N HCl (aq) then saturated NaCl (aq). The aqueous fractions were back-extracted once with EtOAc. The combined organic layers were dried over sodium sulfate, filtered, then concentrated. The resulting residue was purified by silica gel chromatography eluting with 0-60% (DCM/MTBE)/hexanes to afford the title compound. This diastereomer was resolved to provide enantiopure material by HPLC on a Chiralcel IA column (2 cm×25 cm) eluting with 9 mL/min of 3% IPA/n-heptane. LC2 1.54 min. (M-tBu+H)$^+$ 606.

Step C. N-(4-{1-[[7-Chloro-1-methyl-5-(trifluoromethyl)-1H-indazol-3-yl](4-chlorophenyl)methyl]butyl}benzoyl)-β-alanine

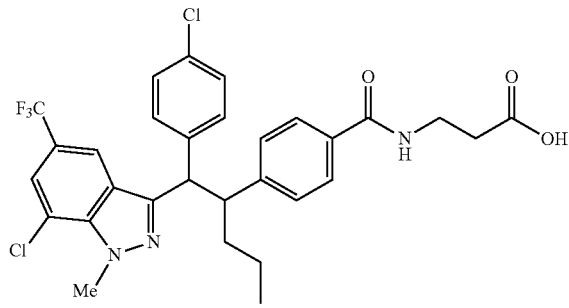

To a solution of the slower-eluting enantiomer of the product from Step B (4.6 mg, 0.0069 mmol) in DCM (1 mL) was added TFA (1 mL, 13 mmol), and the solution was stirred for 30 minutes at RT. The solution was concentrated, then the residue was purified by reverse phase HPLC eluting with acetonitrile/water+0.1% TFA. Following lyophilization, this afforded the enantiopure title compound as a white solid. $^1$H NMR (500 MHz, CD$_3$OD): δ 7.92 (s, 1H); 7.62 (d, J=8.5 Hz, 2H); 7.53 (d, J=8.3 Hz, 2H); 7.43 (s, 1H); 7.36 (d, J=8.2 Hz, 2H); 7.33 (d, J=8.5 Hz, 2H); 4.78 (d, 3=11.5 Hz, 1H); 4.26 (s, 3H); 3.72 (td, J=11.4, 3.2 Hz, 1H); 3.52 (t, J=6.9 Hz, 2H); 2.55 (t, J=6.9 Hz, 2H); 1.68-1.57 (m, 1H); 1.50-1.43 (m, 1H); 1.05-0.97 (m, 2H); 0.73 (t, J=7.3 Hz, 3H); LC2 1.31 min. (M+H)$^+$ 606.

EXAMPLE 3

N-[4-(1-{(4-Chlorophenyl)[7-Chloro-2-Phenyl-5-(Trifluoromethyl)-2H-Indazol-3-Yl]Methyl}Butyl)Benzoyl]-β-Alanine

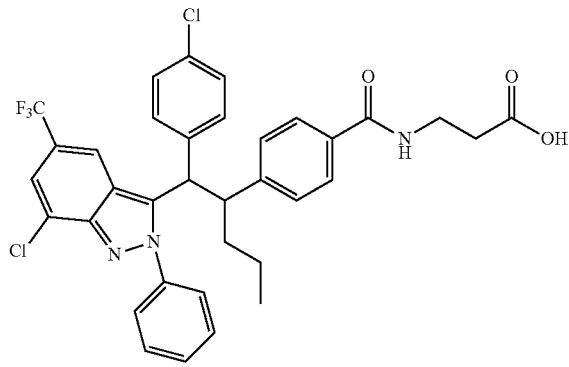

Step A. tert-Butyl N-[4-(1-{(4-chlorophenyl)[7-chloro-2-phenyl-5-(trifluoromethyl)-2H-indazol-3-yl]methyl}butyl)benzoyl]-β-alaninate

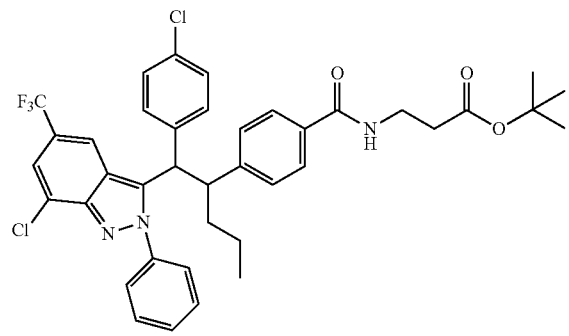

To a solution of the major diastereomer of tert-butyl N-(4-{1-[2-[3-chloro-2-fluoro-5-(trifluoromethyl)phenyl]-1-(4-chlorophenyl)-2-oxoethyl]butyl}benzoyl)-β-alaninate (EXAMPLE 2, Step A, 100 mg, 0.153 mmol) in pyridine (1.5 mL) was added phenylhydrazine (0.083 mL, 0.076 mmol). The mixture was stirred at 80° C. for 18 hours in a sealed tube. The mixture was diluted with EtOAc then washed with 2 N HCl (aq) then saturated NaCl (aq). The organic layer was dried over sodium sulfate, filtered, then concentrated. The resulting residue was purified by silica gel chromatography eluting with 0-50% EtOAc/hexanes to afford the title compound. This diastereomer was resolved to provide enantiopure material by HPLC on a ChiralPak IA column (2 cm×25 cm) eluting with 9 mL/min of 5% EtOH/n-heptane. LC1 2.98 min. (M-tBu+H)$^+$ 668.

Step B. N-[4-(1-{(4-Chlorophenyl)[7-chloro-2-phenyl-5-(trifluoromethyl)-2H-indazol-3-yl]methyl}butyl)benzoyl]-β-alanine

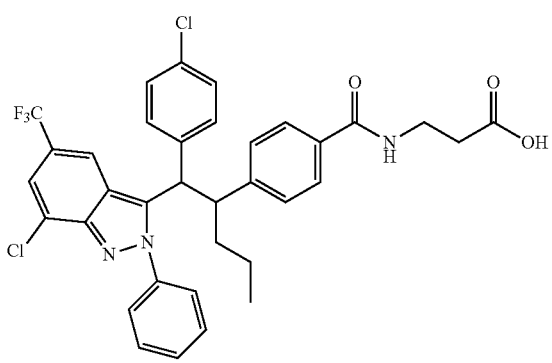

To a solution of the faster-eluting enantiomer of the product from Step B (34 mg, 0.047 mmol) in DCM (1 mL) was added TFA (1 mL, 13 mmol), and the solution was stirred for 30 minutes at RT. The solution was concentrated, then the residue was purified by reverse phase HPLC eluting with acetonitrile/water+0.1% TFA. Following lyophilization, this afforded the enantiopure title compound as a white solid. $^1$H NMR (500 MHz, CD$_3$OD): δ 8.64 (s, 1H); 7.74-7.68 (m, 1H); 7.68-7.62 (m, 2H); 7.56-7.52 (m, 3H); 7.38 (d, J=8.4 Hz, 2H); 7.33 (d, J=8.4 Hz, 2H); 7.12-7.06 (m, 4H); 4.49 (d, J=11.92 Hz, 1H); 3.96 (td, J=11.11, 3.45 Hz, 1H); 3.54 (t, J=6.94 Hz, 2H); 2.60-2.54 (m, 2H); 1.52-1.36 (m, 2H); 1.08-0.86 (m, 2H); 0.68 (t, J=7.3 Hz, 3H); LC1 2.69 min. (M+H)$^+$ 668.

EXAMPLE 4

N-[4-(1-{(4-Chlorophenyl)[7-Chloro-2-Methyl-5-(Trifluoromethyl)-2H-Indazol-3-Yl]Methyl}Butyl)Benzoyl]-β-Alanine

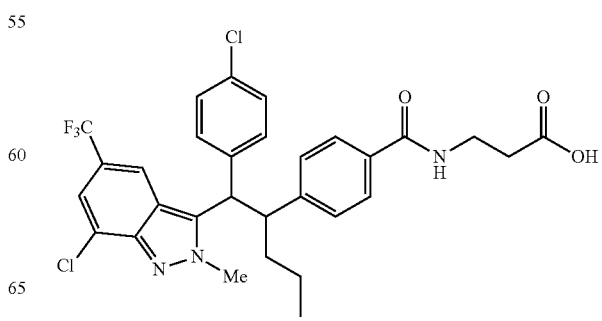

Step A. tert-Butyl N-[4-(1-{(4-chlorophenyl)[7-chloro-5-(trifluoromethyl)-1H-indazol-3-yl]methyl}butyl)benzoyl]-β-alaninate

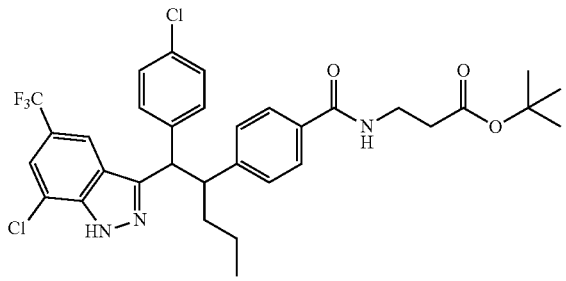

To a solution of the minor diastereomer of tert-butyl N-(4-{1-[2-[3-chloro-2-fluoro-5-(trifluoromethyl)phenyl]-1-(4-chlorophenyl)-2-oxoethyl]butyl}benzoyl)-β-alaninate (EXAMPLE 2, Step A, 71 mg, 0.108 mmol) in pyridine (5 mL) was added hydrazine hydrate (0.053 mL, 1.1 mmol). The mixture was stirred at 80° C. for one hour in a sealed tube. The mixture was diluted with 1 N HCl (aq), then extracted twice with EtOAc. The combined organic layers were dried over sodium sulfate, filtered, then concentrated to afford the title compound. This material was used directly in the next step without further purification. LC2 1.57 min. (M-tBu+H)+ 592.

Step B. tert-Butyl N-[4-(1-{(4-chlorophenyl)[7-chloro-2-methyl-5-(trifluoromethyl)-2H-indazol-3-yl]methyl}butyl)benzoyl]-β-alaninate

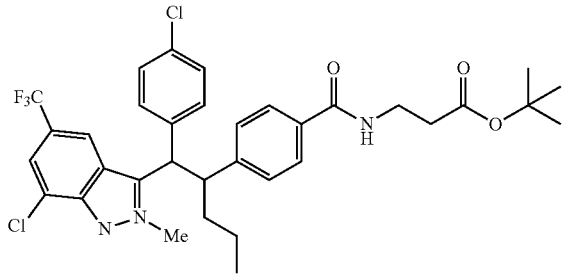

To a solution of the product of Step A (59 mg, 0.091 mmol) in NMP (3 mL) was added Cs$_2$CO$_3$ (38.5 mg, 0.118 mmol) then MeI (0.007 mL, 0.1 mmol). After being stirred at RT for one hour, the mixture was diluted with saturated NaCl (act) then extracted twice with EtOAc. The combined organic layers were dried over sodium sulfate, filtered, then concentrated. The resulting residue was purified by silica gel chromatography eluting with 0-20% MeOH/DCM, then further purified by PTLC eluting with 50% EtOAc/hexanes to afford the 1-methyl regioisomer (EXAMPLE 2, Step B) as well as the title compound. The title compound was resolved to provide enantiopure material by HPLC on a ChiralPak IA (2 cm×25 cm) column eluting with 9 mL/min of 3% EtOH/n-heptane. LC1 2.83 min. (M-tBu+H)+ 606.

Step C. N-[4-(1-{(4-Chlorophenyl)[7-chloro-2-methyl-5-(trifluoromethyl)-2H-indazol-3-yl]methyl}butyl)benzoyl]-β-alanine

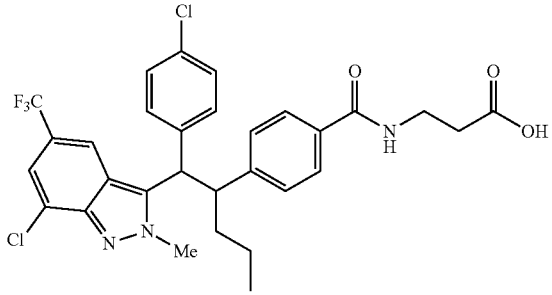

To a solution of the faster-eluting enantiomer of the product from Step B (4 mg, 0.006 mmol) in DCM (1 mL) was added TFA (1 mL, 13 mmol), and the solution was stirred for 30 minutes at RT. The solution was concentrated, then the residue was purified by reverse phase HPLC eluting with acetonitrile/water+0.1% TFA. Following lyophilization, this afforded the enantiopure title compound as a white solid. This was the most potent glucagon receptor antagonist of the four stereoisomeric compounds. $^1$H NMR (600 MHz, CD$_3$OD): δ 8.44 (s, 1 H); 7.60 (d, J=8.3 Hz, 2H); 7.52 (d, J=8.0 Hz, 2H); 7.40 (d, J=8.3 Hz, 2H); 7.39 (s, 1H); 7.32 (d, J=8.0 Hz, 2H); 5.02 (d, J=11.9 Hz, 1H); 4.07 (s, 3H); 4.02 (td, J=11.3, 3.4 Hz, 1H); 3.51 (t, J=7.0 Hz, 2H); 2.54 (t, J=7.0 Hz, 2H); 1.76-1.61 (m, 2H); 1.19-1.02 (m, 2H); 0.78 (t, J=7.3 Hz, 3H); LC1 2.44 min. (M+H)− 606.

Using the chemistry described for the preparation of INTERMEDIATE 1 and in EXAMPLES 1-4, the compounds in TABLES 1 and 2 were prepared as enantiopure compounds. The data listed are for the most active stereoisomer that was prepared. The R$^3$ groups that are shown in TABLES 1 and 2 are specified when they represent a value other than a hydrogen atom. The remaining R$^3$ groups that are unspecified are hydrogen atoms.

TABLE 1

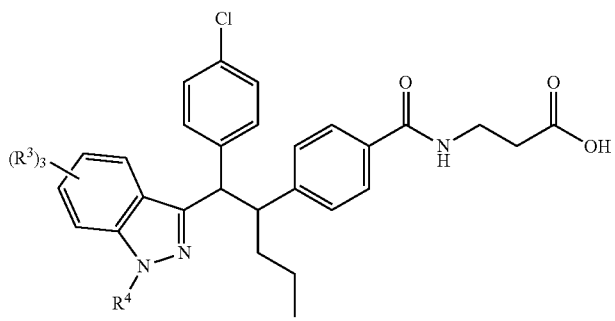

| EXAMPLE | R$^3$ | R$^4$ | LC-MS Data |
|---|---|---|---|
| 5 | 5-CF$_3$ | H | LC2, 1.43 min. (M + H)+ 558 |

N-[4-(1-{(4-CHLOROPHENYL)[5-(TRIFLUOROMETHYL)-1H-INDAZOL-3-YL]METHYL}BUTYL)BENZOYL]-β-ALANINE

TABLE 1-continued

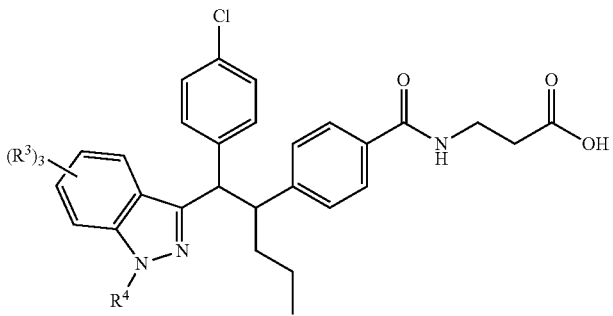

| EXAMPLE | R³ | R⁴ | LC-MS Data |
|---|---|---|---|
| 6 | 5-CF₃, 7-Cl | H | LC2, 1.26 min. (M + H)⁺ 592 |
| | N-[4-(1-{(4-CHLOROPHENYL)[7-CHLORO-5-(TRIFLUOROMETHYL)-1H-INDAZOL-3-YL]METHYL}BUTYL)BENZOYL]-β-ALANINE | | |
| 7 | 5-F, 7-F | H | LC2, 1.18 min. (M + H)⁺ 526 |
| | N-[4-(1-{(4-CHLOROPHENYL)[5,7-DIFLUORO-1H-INDAZOL-3-YL]METHYL}BUTYL)BENZOYL]-β-ALANINE | | |
| 8 | 5-Cl, 7-Cl | H | LC2, 1.28 min. (M + H)⁺ 558/560 |
| | N-[4-(1-{(4-CHLOROPHENYL)[5,7-DICHLORO-1H-INDAZOL-3-YL]METHYL}BUTYL)BENZOYL]-β-ALANINE | | |
| 9 | 5-CF₃ | Me | LC2, 1.28 min. (M + H)⁺ 572 |
| | N-[4-(1-{(4-CHLOROPHENYL)[1-METHYL-5-(TRIFLUOROMETHYL)-1H-INDAZOL-3-YL]METHYL}BUTYL)BENZOYL]-β-ALANINE | | |
| 10 | 5-F, 7-F | Me | LC2, 1.26 min. (M + H)⁺ 540 |
| | N-[4-(1-{(4-CHLOROPHENYL)[1-METHYL-5,7-DIFLUORO-1H-INDAZOL-3-YL]METHYL}BUTYL)BENZOYL]-β-ALANINE | | |
| 11 | 5-Cl, 7-Me | Me | LC2, 1.47 min. (M + H)⁺ 552 |
| | N-[4-(1-{(4-CHLOROPHENYL)[1,7-DIMETHYL-5-CHLORO-1H-INDAZOL-3-YL]METHYL}BUTYL)BENZOYL]-β-ALANINE | | |
| 12 | 5-Cl, 7-Cl | Me | LC2, 1.32 min. (M + H)⁺ 572/574 |
| | N-[4-(1-{(4-CHLOROPHENYL)[1-METHYL-5,7-DICHLORO-1H-INDAZOL-3-YL]METHYL}BUTYL)BENZOYL]-β-ALANINE | | |

TABLE 2

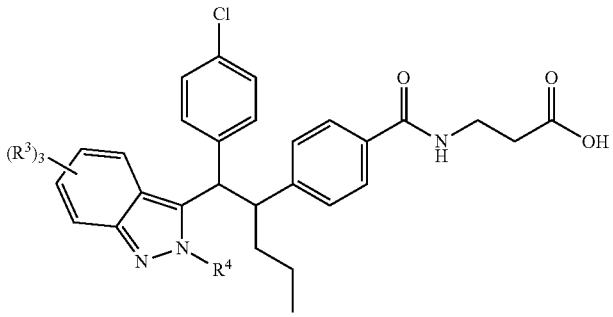

| EXAMPLE | R³ | R⁴ | LC-MS Data |
|---|---|---|---|
| 13 | 5-CF₃ | Me | Not Obtained |
| | ¹H NMR (500 MHz, CD₃OD): δ 8.47 (s, 1 H); 7.74 (d, J = 8.9 Hz, 1 H); 7.67 (d, J = 8.2 Hz, 2 H); 7.51 (d, J = 8.9 Hz, 1 H); 7.41 (d, J = 8.3 Hz, 2 H); 7.11 (d, J = 8.5 Hz, 2 H); 7.06 (d, J = 8.7 Hz, 2 H); 4.87 (obs, 1 H); 4.17 (s, 3 H); 4.04 (td, J = 11.7, 3.0 Hz, 1 H); 3.59 (t, J = 6.8 Hz, 2 H); 2.61 (t, J = 6.8 Hz, 2 H); 1.81-1.72 (m, 1 H); 1.63-1.55 (m, 1 H); 1.12-1.04 (m, 2 H); 0.73 (t, J = 7.4 Hz, 3 H). | | |
| | N-[4-(1-{(4-CHLOROPHENYL)[2-METHYL-5-(TRIFLUOROMETHYL)-2H-INDAZOL-3-YL]METHYL}BUTYL)BENZOYL]-β-ALANINE | | |
| 14 | 5-CF₃, 7-Cl | Et | LC1, 2.58 min. (M + H)⁺ 620 |
| | N-[4-(1-{(4-CHLOROPHENYL)[7-CHLORO-2-ETHYL-5-(TRIFLUOROMETHYL)-2H-INDAZOL-3-YL]METHYL}BUTYL)BENZOYL]-β-ALANINE | | |
| 15 | 5-CF₃, 7-Cl | n-Pr | LC2, 1.50 min. (M + H)⁺ 634 |
| | N-[4-(1-{(4-CHLOROPHENYL)[7-CHLORO-2-n-PROPYL-5-(TRIFLUOROMETHYL)-2H-INDAZOL-3-YL]METHYL}BUTYL)BENZOYL]-β-ALANINE | | |

TABLE 2-continued

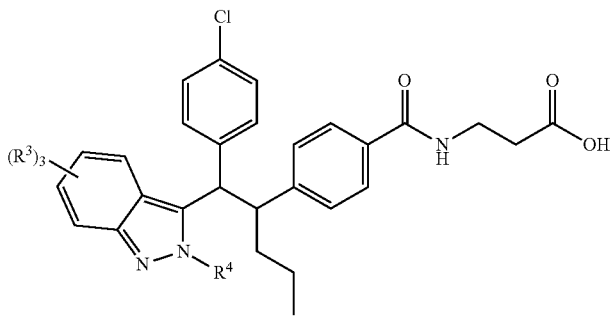

| EXAMPLE | R³ | R⁴ | LC-MS Data |
|---|---|---|---|
| 16 | 5-CF₃, 7-Cl | i-Pr | LC1, 2.65 min. (M + H)⁺ 634 |
| | N-[4-(1-{(4-CHLOROPHENYL)[7-CHLORO-2-ISOPROPYL-5-(TRIFLUOROMETHYL)-2H-INDAZOL-3-YL]METHYL}BUTYL)BENZOYL]-β-ALANINE | | |
| 17 | 5-CF₃, 7-Cl | —CH₂CF₃ | LC1, 2.62 min. (M + H)⁺ 674 |
| | N-[4-(1-{(4-CHLOROPHENYL)[7-CHLORO-2-(2,2,2-TRIFLUOROETHYL)-5-(TRIFLUOROMETHYL)-2H-INDAZOL-3-YL]METHYL}BUTYL)BENZOYL]-β-ALANINE | | |
| 18 | 5-F, 7-F | Me | LC2, 1.26 min. (M + H)⁺ 540 |
| | N-[4-(1-{(4-CHLOROPHENYL)[2-METHYL-5,7-DIFLUORO-2H-INDAZOL-3-YL]METHYL}BUTYL)BENZOYL]-β-ALANINE | | |
| 19 | 5-Cl, 7-Cl | Me | LC2, 1.38 min. (M + H)⁺ 572/574 |
| | N-[4-(1-{(4-CHLOROPHENYL)[2-METHYL-5,7-DICHLORO-2H-INDAZOL-3-YL]METHYL}BUTYL)BENZOYL]-β-ALANINE | | |
| 20 | 5-Cl, 7-Me | Me | LC2, 1.41 min. (M + H)⁺ 552 |
| | N-[4-(1-{(4-CHLOROPHENYL)[5-CHLORO-2,7-DIMETHYL-2H-INDAZOL-3-YL]METHYL}BUTYL)BENZOYL]-β-ALANINE | | |

EXAMPLE 21

N-[4-(1-{(4-Chlorophenyl)[7-Fluoro-5-(4-Methylphenyl)-1H-Indazol-3-Yl]Methyl}Butyl)Benzoyl]-β-Alanine

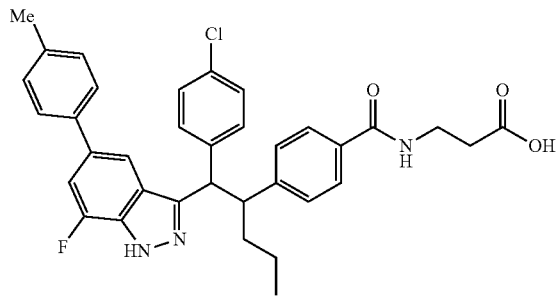

Step A.
(6-Bromo-2,3-difluorophenyl)(trimethyl)silane

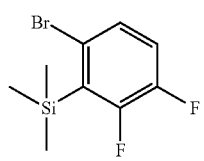

Diisopropylamine (2.62 g, 25.9 mmol) was added drop wise to a solution of n-BuLi (2.5 M in hexane, 10.4 mL, 26.0 mmol) in anhydrous THF (19 mL) at −78° C., then the solution was stirred at −78° C. for 15 minutes. To this solution was added 4-bromo-1,2-difluorobenzene (5.00 g, 25.9 mmol), then the mixture was stirred at −78° C. for 2 hours. Freshly distilled chlorotrimethylsilane (2.81 g, 25.9 mmol) was added, then the mixture was allowed to warm to room temperature slowly over two hours. The mixture was diluted with saturated NaCl (aq) then extracted with EtOAc (3×40 mL). The combined organic layers were dried over MgSO₄, filtered, then concentrated to afford the title compound as a light yellow oil. This material was used directly in the next step without further purification. ¹H NMR (500 MHz, CDCl₃): δ 7.27 (ddd, J=8.7, 4.0, 1.7 Hz, 1H); 7.00 (q, J=8.9 Hz, 1H); 0.47 (s, 9H).

Step B.
5-Bromo-2,3-difluoro-4-(trimethylsilyl)benzoic acid

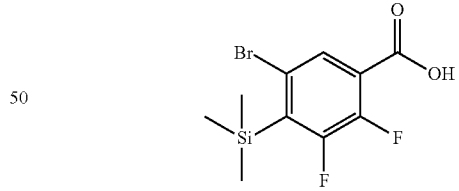

To a solution of n-BuLi (2.0 M in hexanes, 11.1 mL, 22.2 mmol) in anhydrous THF (17 mL) at −78° C. was added drop wise 2,2,6,6-tetramethylpiperidine (3.26 g, 22.1 mmol). After being stirred for 15 minutes, a solution of the product from step A (5.86 g, 22.1 mmol) in THF (20 mL) was added. The reaction mixture was stirred at −78° C. for 2 hours, then dry ice (100 g) was added. The mixture was allowed to stand at room temperature overnight, then it was diluted with water and extracted with EtOAc. The combined organics were dried over MgSO₄, filtered, then concentrated to afford the title compound. The material was used directly in the next step without further purification. ¹H NMR (500 MHz, CDCl₃): δ 7.70 (d, J=4.4 Hz, 1H); 0.44 (s, 9H).

Step C. Methyl 5-bromo-2,3-difluoro-4-(trimethylsilyl)benzoate

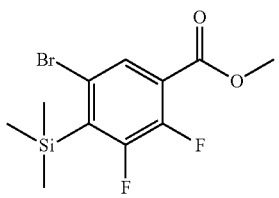

Sulfuric acid (1.88 mL, 22.3 mmol) was added to a solution of the benzoic acid from step B (5.3 g, 17.1 mmol) in methanol (34 mL) at room temperature. The resulting mixture was stirred at reflux overnight. The mixture was allowed to cool to room temperature then concentrated. The resulting residue was dissolved in EtOAc then washed with saturated NaHCO$_3$ (aq), water, then saturated NaCl (aq). The organics were dried over MgSO$_4$, filtered, then concentrated. The resulting residue was purified by silica gel chromatography eluting with 0-10% MeOH/CH$_2$Cl$_2$ to afford the title compound as a white solid. $^1$H NMR (600 MHz, CDCl$_3$): δ 7.78 (dd, J=5.4, 1.0 Hz, 1H); 3.93 (s, 3H); 0.43 (s, 9H).

Step D. 1-[5-bromo-2,3-difluoro-4-(trimethylsilyl)phenyl]-2-(4-chlorophenyl)ethanone

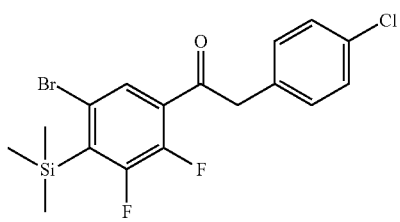

To a solution of NaHMDS (1.0 M in THF, 7.7 mL, 7.7 mmol) in anhydrous THF (25 mL) at −78° C. was added a solution of 4-chlorophenylacetic acid (0.528 g, 3.09 mmol) in anhydrous THF (25 mL) over 10 minutes. The solution was stirred for 5 minutes, then a solution of the product of Step C (4.16 g, 7.8 mmol) in THF (25 mL) was added drop wise over 10 minutes. The mixture was stirred at −78° C. for two hours. The mixture was diluted with 2N HCl (aq, 50 mL), then the product was extracted into EtOAc. The organics were dried over Na$_2$SO$_4$, filtered, then concentrated. The resulting residue was purified by silica gel chromatography eluting with 0-50% toluene/hexanes to afford the title compound. $^1$H NMR (600 MHz, CDCl$_3$): δ 7.74 (dd, J=5.3, 1.8 Hz, 1H); 7.31 (d, J=8.2 Hz, 2H); 7.16 (d, J=8.5 Hz, 2H); 4.22 (s, 2H); 0.48 (s, 9H).

Step E. tert-Butyl 4-{1-[2-(5-bromo-2,3-difluorophenyl)-1-(4-chlorophenyl)-2-oxoethyl]butyl}benzoate

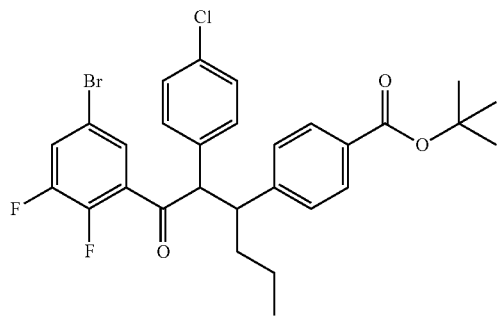

To a suspension of NaH (60 wt % in mineral oil, 0.129 g, 3.23 mmol) in DMF (5 mL) at 0° C. was add a solution of the product from Step D (0.900 g, 2.15 mmol) in DMF (2 mL). The suspension was stirred for 30 minutes, then a solution of tert-butyl 4-(1-bromobutyl)benzoate (0.742 g, 2.37 mmol) in DMF (2 mL) was added. The mixture was stirred at 0° C. for two hours then diluted with saturated NaCl (aq, 50 mL), then the product was extracted with EtOAc (3×30 mL). The combined organic extracts were washed with water then saturated NaCl (aq), dried over MgSO$_4$, filtered, then concentrated. The resulting residue was purified by silica gel chromatography eluting with 0-50% toluene/hexanes to afford racemic mixtures of both diastereomers of the title compound.

Faster-eluting diastereomer: $^1$H NMR (600 MHz, CDCl$_3$): δ 7.76 (d, J=8.3 Hz, 2H); 7.62 (dd, J=4.7, 2.3 Hz, 1H); 7.47 (ddd, J=8.8, 6.7, 2.5 Hz, 1H); 7.04 (d, J=8.5 Hz, 2 H); 7.02 (d, J=8.3 Hz, 2H); 6.95 (d, J=8.4 Hz, 2H); 4.64 (d, J=10.8 Hz, 1H); 3.63-3.55 (m, 1H); 1.80-1.72 (m, 1H); 1.72-1.63 (m, 1H); 1.57 (s, 9H); 1.18-0.99 (m, 2H); 0.82 (t, J=7.3 Hz, 3H).

Slower-eluting diastereomer: $^1$H NMR (600 MHz, CDCl$_3$): δ 7.88 (d, J=8.0 Hz, 2H); 7.36-7.33 (m, 4H); 7.31 (d, J=8.1 Hz, 2H); 7.15 (dd, J=4.9, 2.4 Hz, 1H); 7.04 (t, J=7.5 Hz, 1H); 4.73 (d, J=11.0 Hz, 1H); 3.48 (t, J=11.2 Hz, 1H); 1.45-1.26 (m, 2H); 1.26 (s, 9H); 1.01-0.87 (m, 2H); 0.69 (t, J=7.3 Hz, 3H).

Step F. tert-Butyl N-(4-{1-[2-(5-bromo-2,3-difluorophenyl)-1-(4-chlorophenyl)-2-oxoethyl]butyl}benzoyl)-β-alaninate

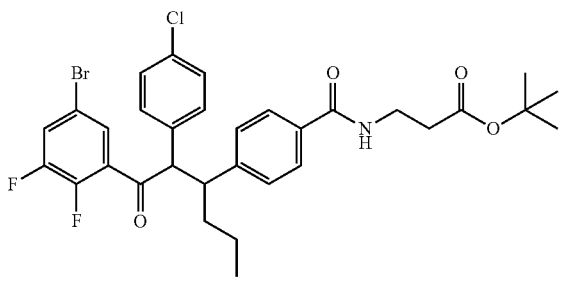

To a solution of a mixture of the two diastereomeric products of step E (1.00 g, 1.73 mmol) in DCM (10 mL) at 0° C. was added TFA (10 mL, 130 mmol) over one minute. Once all ester starting material had been consumed by LC/MS analysis, the solution was concentrated to afford the title compound. After being dried on high vacuum, the material was used directly in the next step without further purification.

To a solution of the product of the previous step (190 mg, 0.329 mmol), tert-butyl-β-alaninate hydrochloride (59.7 mg, 0.329 mmol), EDC (63.0 mg, 0.329 mmol), and HOBt (5.0 mg, 0.33 mmol) in DMF (4 mL) was added Et$_3$N (0.23 mL, 1.6 mmol), then the mixture was stirred at room temperature overnight. The mixture was diluted with ethyl acetate then washed with water then saturated NaCl (aq). The organic layer was dried over sodium sulfate, filtered, then concentrated. The residue was purified by silica gel chromatography eluting with 0-30% EtOAc/hexanes to afford the title compound. LC3 1.44 min. (M−H)$^-$ 648.

Step G. tert-Butyl N-(4-{1-](5-bromo-7-fluoro-1H-indazol-3-yl)(4-chlorophenyl)methyl]butyl}benzoyl)-β-alaninate

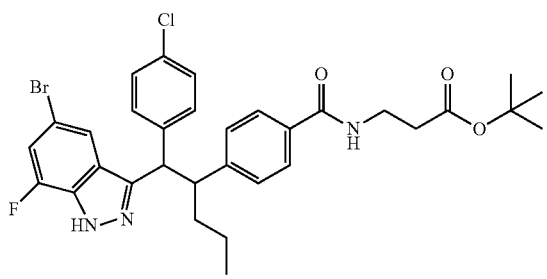

To a solution of the product of Step F (600 mg, 0.925 mmol) in DMSO (10 mL) was added hydrazine hydrate (60 wt %, 2.0 mL, 24 mmol). The mixture was stirred at room temperature until all starting ketone had been consumed by LC-MS analysis. The mixture was diluted with ethyl acetate then washed with saturated NaCl (aq). The organic layer was dried over sodium sulfate, filtered, then concentrated. The resulting residue was purified by silica gel chromatography eluting with 0-50% EtOAc/hexanes to afford the title compound as a solid. LC2 1.40 min. (M+H)$^+$644.

Step H. tert-Butyl 5-bromo-3-[2-(4-{[(3-tert-butoxy-3-oxopropyl)amino[carbonyl}phenyl)-1-(4-chlorophenyl)pentyl]-7-fluoro-1H-indazole-1-carboxylate

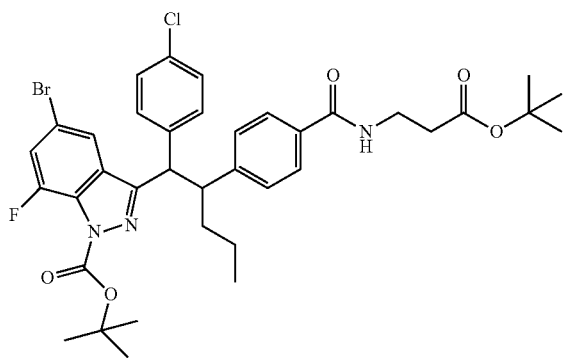

To a solution of the product of step G (223 mg, 0.347 mmol) in DMF (5 mL) at 0° C. was added cesium carbonate (136 mg, 0.416 mmol) and di-tert-butyl dicarbonate (114 mg, 0.520 mmol). The mixture was allowed to warm to room temperature and was stirred for two hours. The mixture was diluted with EtOAc (30 mL) then washed with water then saturated NaCl (aq). The organic layer was dried over MgSO$_4$, filtered, then concentrated. The resulting residue was purified by silica gel chromatography eluting with 0-30% EtOAc/hexanes to afford the title compound. LC1 2.85 min. (M+H)$^+$744.

Step I. N-[4-(1-{(4-Chlorophenyl)[7-fluoro-5-(4-methylphenyl)-1H-indazol-3-yl]methyl}butyl)benzoyl]-β-alanine

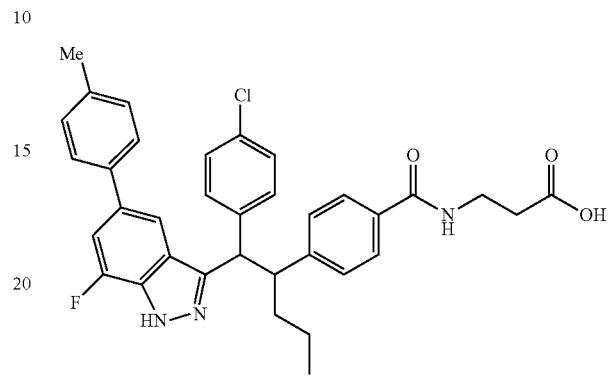

To a solution of the product of step H (50 mg, 0.067 mmol) in a mixture of THF (0.5 mL) and water (0.5 mL), was added 4-methylphenyl boronic acid (13.7 mg, 0.101 mmol), tetrakis(triphenyl phosphine)palladium(0) (31.1 mg, 0.027 mmol), and sodium carbonate (10.7 mg, 0.101 mmol). The mixture was purged with nitrogen then heated in a microwave reactor at 120° C. for one hour. The mixture was diluted with EtOAC then washed with water then saturated NaCl (aq). The organic layer was dried over sodium sulfate, filtered, then concentrated. The resulting material was used directly in the next step.

The product of the previous step was dissolved in CH$_2$Cl$_2$ (1.0 mL), then TFA (1.0 mL) was added. The solution was stirred at room temperature for one hour then concentrated. The resulting residue was purified, and the diastereomers were separated, by reverse phase HPLC eluting with acetonitrile/water+0.1% TFA. Following lyophilization, this afforded racemic mixtures of the two diastereomers of the title compound.

Faster-eluting Diastereomer: $^1$H NMR (600 MHz, CDCl$_3$): δ 7.70-7.60 (m, 3H); 7.48 (d, J=7.8 Hz, 2H); 7.36 (d, J=11.7 Hz, 1H); 7.31-7.26 (m, 2H); 7.23-7.19 (m, 2H); 7.12 (d, J=8.2 Hz, 2H); 7.00 (d, J=8.1 Hz, 2H); 6.92 (d, J=7.1 Hz, 1H); 4.62 (d, J=11.2 Hz, 1H); 3.83-3.71 (m, 3H); 2.77-2.71 (m, 2H); 2.43 (s, 3H); 1.79-1.69 (m, 1H); 1.66-1.57 (m, 1H); 1.12-0.96 (m, 2H); 0.70 (t, J=7.4 Hz, 3H); LC3 1.33 min. (M−H)$^−$ 596.

Slower-eluting Diastereomer: This diastereomer was the more potent glucagon receptor antagonist. $^1$H NMR (600 MHz, CDCl$_3$): δ 7.53-7-47 (m, 3H); 7.47-7.40 (m, 4H); 7.32-7.20 (m, 7H); 6.86 (br, 1H); 4.66 (d, J=11.6 Hz, 1H); 3.81-3.67 (m, 2H); 3.66-3.57 (m, 1H); 2.67 (br 2H); 2.44 (s, 3H); 1.61-1.44 (m, 2H); 1.07-0.96 (m, 2H); 0.74 (t, J=7.3 Hz, 3H); LC3 1.35 min. (M−H)$^−$ 596.

Using the chemistry described in EXAMPLE 21, the compounds in TABLE 3 were prepared as racemic mixtures. The data provided are for the diastereomer that is the more potent glucagon receptor antagonist.

TABLE 3
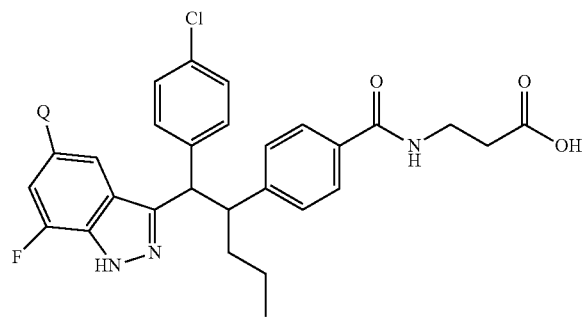
| EXAMPLE | Q | LC-MS Data |
|---|---|---|
| 22 | Br | LC1, 2.20 min. (M + H)+ 588 |
| 23 | H | LC1, 2.17 min. (M + H)+ 508 |
| 24 | 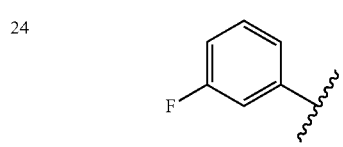 | LC3, 1.34 min. (M − H)− 600 |
| 25 | 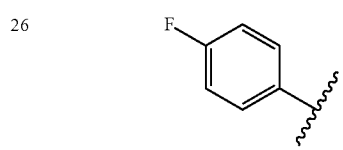 | LC3, 1.31 min. (M − H)− 582 |
| 26 | 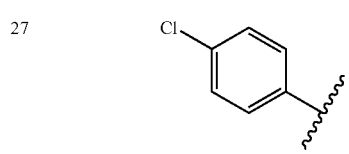 | LC3, 1.34 min. (M − H)− 600 |
| 27 | 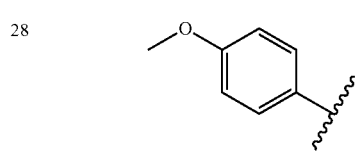 | LC3, 1.35 min. (M − H)− 616 |
| 28 | 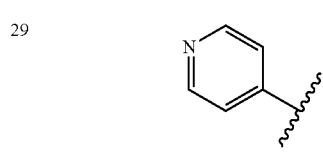 | LC3, 1.32 min. (M − H)− 612 |
| 29 | 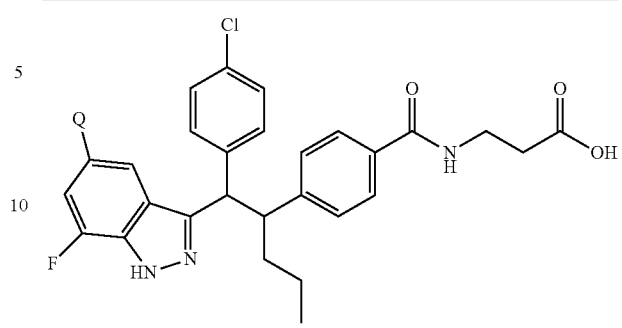 | LC3, 1.13 min. (M − H)− 583 |
TABLE 3-continued
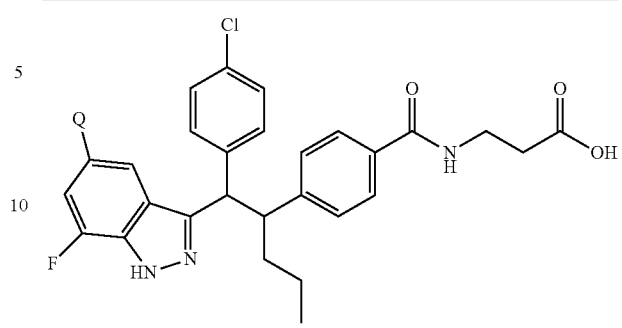
| EXAMPLE | Q | LC-MS Data |
|---|---|---|
| 30 | 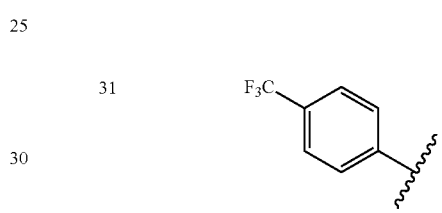 | LC3, 1.25 min. (M − H)− 660 |
| 31 |  | LC3, 1.32 min. (M − H)− 650 |
| 32 |  | LC3, 1.39 min. (M − H)− 666 |
| 33 | | LC3, 1.34 min. (M − H)− 630 |
| 34 | | LC3, 1.32 min. (M − H)− 646 |
| 35 | | LC3, 1.34 min. (M − H)− 618 |

EXAMPLE 36

N-(4-{1-[(4-Chlorophenyl)(5-Cyano-7-Fluoro-1H-Indazol-3-Yl)Methyl]Butyl}Benzoyl)-β-Alanine

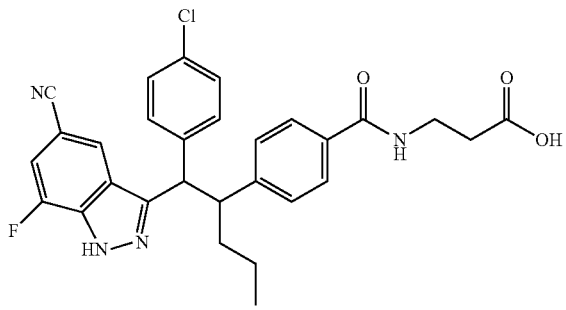

To a solution of tert-butyl 5-bromo-3-[2-(4-{[(3-tert-butoxy-3-oxopropyl)amino]carbonyl}phenyl)-1-(4-chlorophenyl)pentyl]-7-fluoro-1H-indazole-1-carboxylate (EXAMPLE 21, Step H, 100 mg, 0.135 mmol) in DMF (2 mL) was added zinc (II) cyanide (17.4 mg, 0.148 mmol) and tetrakis(triphenylphosphine)palladium (0) (31 mg, 0.027 mmol). The mixture was purged with nitrogen then stirred at 120° C. overnight. After being allowed to cool to room temperature, the mixture was diluted with ethyl acetate then washed with water then saturated NaCl (aq). The organic layer was dried over sodium sulfate, filtered, then concentrated. The resulting residue was purified, and the diastereomers were separated, by silica gel chromatography eluting with 0-20% EtOAc/toluene.

Each diastereomer was independently dissolved in $CH_2Cl_2$ (1.0 mL) then treated with TFA (1.0 mL). After being stirred at room temperature for two hours, the solutions were concentrated. The residues were purified by reverse phase HPLC eluting with acetonitrile/water+0.1% TFA. Following lyophilization, this afforded racemic mixtures of the two diastereomers of the title compound.

Diastereomer A (from the faster-eluting t-butyl ester precursor): $^1$H NMR (500 MHz, $CDCl_3$): δ 7.89 (s, 1H); 7.63 (d, J=7.9 Hz, 2H); 7.35-7.26 (m, 1H); 7.20 (d, J=7.9 Hz, 2H); 7.11 (d, J=8.3 Hz, 2H); 7.05 (d, J=8.3 Hz, 2H); 6.90-6.84 (m, 1H); 4.57 (d, J=10.9 Hz, 1H); 3.84-3.73 (m, 3H); 2.79-2.74 (m, 2H); 1.75-1.55 (m, 2H); 1.14-1.00 (m, 2H); 0.74 (t, J=7.3 Hz, 3H); LC1 2.75 min. $(M+H)^+$ 533.

Diastereomer B (from the slower-eluting t-butyl ester precursor): This diastereomer was the more potent glucagon receptor antagonist. $^1$H NMR (500 MHz, $CDCl_3$): δ 7.76 (s, 1H); 7.58-7.52 (m, 2H); 7.49-7.43 (m, 2H); 7.35 (d, J=8.0 Hz, 2H); 7.29 (m, 2H); 7.17-7.10 (m, 1H); 6.91 (m, 1H); 4.60 (d, 3=11.7 Hz, 1H); 3.77 (m, 1H); 3.69 (m, 2H); 2.68 (m, 2H); 1.60 (m, 2H); 1.03 (m, 2H); 0.77 (t, J=7.4 Hz, 3H); LC1 2.81 $(M+H^+$ 533.

EXAMPLE 37

N-(4-{(1S)-1-[(R)-(4-Chlorophenyl)(7-Fluoro-5-Methyl-1H-Indazol-3-Yl)Methyl]Butyl}Benzoyl)-β-Alanine

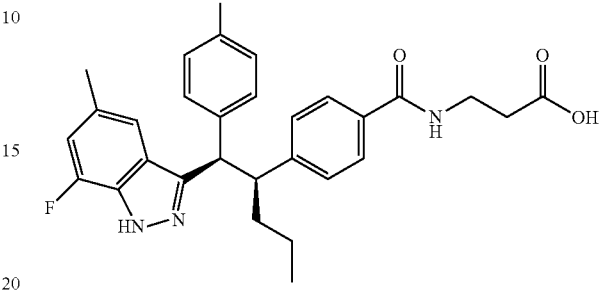

Step A. N-(4-{(1S)-1-[2-(2-amino-3-fluoro-5-methylphenyl)-1-(4-chlorophenyl)-2-oxoethyl]butyl}benzoyl)-β-alanine

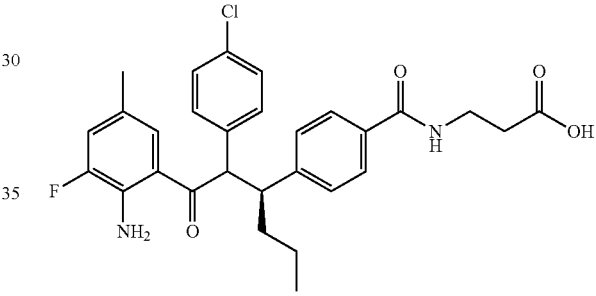

A solution of N-(4-{(1S)-1-[(R)-(4-chlorophenyl)-(7-fluoro-5-methyl-1H-indol-4-yl)methyl]butyl}-benzoyl)-β-alanine (prepared as described in PCT Patent Publication WO 2008/042223 A1 published on 10 Apr. 2008, 455 mg, 0.87 mmol) in methanol (100 mL) was cooled to −78° C. Ozone was bubbled through the solution until the blue color of ozone was observed. Nitrogen was then bubbled through the solution until the blue color of ozone dissipated. Dimethyl sulfide (1.3 mL, 17 mmol) was added, then the mixture was stirred at room temperature overnight then concentrated. The resulting yellow solid was dissolved in EtOAc, washed with water then saturated NaCl (aq), dried over $MgSO_4$, filtered, then concentrated. NMR and LC/MS analysis showed it was a mixture (1:3) of the title compound and the aniline-N-formylated title compound. This mixture was used for the next step without further purification. Title compound: LC1 2.27 min. $(M+H)^+$ 525. Formylated compound: LC1 2.09 min. $(M+H)^+$ 553.

The mixture of products from the previous step (335 mg, 0.606 mmol) was refluxed in THF (20 mL) with HCl (10% in water, 3.0 mL, 9.9 mmol) for one hour. After being allowed to cool to room temperature, the mixture was diluted with saturated $NH_4Cl$ (aq) then extracted with EtOAc. The organic phase was washed with saturated NaCl (aq), dried over $MgSO_4$, filtered, then concentrated. This afforded the title compound as a solid which was used for the next step without further purification. LC1 2.27 min. $(M+H)^+$ 525.

Step B. N-(4-{(1S)-1-[(R)-(4-chlorophenyl)(7-fluoro-5-methyl-1H-indazol-3-yl)methyl]butyl}benzoyl)-β-alanine

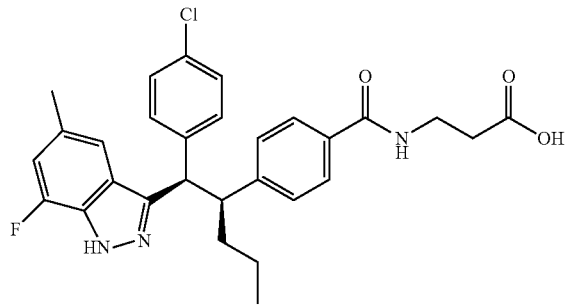

The product from Step A (74 mg, 0.14 mmol) was suspended in concentrated HCl (1 mL) then cooled to 0° C. To the stirred suspension was added a solution of NaNO$_2$ (7.5 mg, 0.11 mmol) in water, then the mixture was stirred for 30 minutes. Solid SnCl$_2$ (47 mg, 0.25 mmol) was added, then the mixture was stirred for another 30 minutes. Ice was added, then the mixture was extracted with EtOAc. The organic phase was washed with water then saturated NaCl(aq), dried over Na$_2$SO$_4$, filtered, then concentrated. The residue was purified by reverse phase HPLC eluting with 10-70% acetonitrile/water+0.1% TFA. Following lyophilization, this afforded the title compound as a white solid. $^1$H NMR (500 MHz, CDCl$_3$): δ 7.51 (d, J=7.9 Hz, 2H); 7.43 (d, J=8.1 Hz, 2H); 7.31 (d, J=8.2 Hz, 2H); 7.26 obs, 2H); 7.17 (s, 1H); 6.85-6.78 (m, 2H); 4.60 (d, J=11.6 Hz, 1H); 3.76-3.62 (m, 3H); 2.70 (t, J=5.6 Hz, 2H); 2.41 (s, 3H); 1.59-1.43 (m, 2H); 1.07-0.96 (m, 2H); 0.73 (t, J=7.3 Hz, 3H). LC1 2.36 min. (M+H)$^+$ 522.

Biological Assays

The ability of the compounds of the present invention to inhibit the binding of glucagon and their utility in treating or preventing type 2 diabetes mellitus and the related conditions can be demonstrated by the following in vitro assays.

Glucagon Receptor Binding Assay

A stable CHO (Chinese hamster ovary) cell line expressing cloned human glucagon receptor was maintained as described (Chicchi, et. al. *J Biol Chem* 272, 7765-9(1997); Cascieri, et. al. *J Biol Chem* 274, 8694-7(1999)). To determine antagonistic binding affinity of compounds, 0.001-0.003 mg of cell membranes from these cells were pre-incubated with 0.100 mg WGA-coated PVT SPA beads (Amersham) for 20 minutes at room temperature in 25 pt of a buffer containing 50 mM Tris-HCl (pH 7.5), 5 mM MgCl$_2$, 2 mM EDTA, 0.1% BSA and 3% glycerol in Costar 384 well plates with clear bottoms (#3706). Next, 25 μL of $^{125}$I-Glucagon (New England Nuclear, MA) (1×10$^{-14}$ mol per well) and either 1 μL solutions of test compounds or 0.001 mM unlabeled glucagon or DMSO were added and mixed. After 4-12 hours incubation at room temperature, the radioactivity bound to the cell membranes was determined in a radioactive emission detection counter (Wallac-Microbeta). Data were analyzed using the Data Analyzer software program of Merck & Co., Inc. The IC$_{50}$ values were calculated using non-linear regression analysis assuming single-site competition. IC$_{50}$ values for the compounds of the invention are generally in the range of as low as about 1 nM to as high as about 500 nM, and thus have utility as glucagon antagonists. When a synthetic example includes the preparation of multiple stereoisomers of a compound, the IC$_{50}$ value shown below in TABLE 4 is for the most active stereoisomer that was prepared.

TABLE 4

| Example | IC$_{50}$ (nM) | Example | IC$_{50}$ (nM) | Example | IC$_{50}$ (nM) |
|---|---|---|---|---|---|
| 1 | 0.6 | 8 | 0.4 | 17 | 3.9 |
| 2 | 0.7 | 9 | 1.0 | 19 | 2.0 |
| 3 | 37 | 10 | 4.0 | 21 | 2.6 |
| 4 | 2.6 | 11 | 0.7 | 24 | 1.7 |
| 5 | 0.8 | 12 | 0.9 | 36 | 4.3 |
| 6 | 0.2 | 13 | 3.3 | 37 | 0.8 |

Inhibition of Glucagon-Stimulated Intracellular cAMP Formation

Exponentially growing CHO cells expressing human glucagon receptor were harvested with the aid of enzyme-free dissociation media (Specialty Media), pelleted at low speed, and re-suspended in the Cell Stimulation Buffer included in the Flash Plate cAMP kit (New England Nuclear, SMP0004A). The adenylate cyclase assay was conducted as per manufacturer instructions. Briefly, compounds were diluted from stocks in DMSO and added to cells at a final DMSO concentration of 5%. Cells prepared as above were preincubated in flash plates coated with anti-cAMP antibodies (NEN) in the presence of compounds or DMSO controls for 30 minutes, then stimulated with glucagon (250 pM) for an additional 30 minutes. The cell stimulation was stopped by addition of equal amounts of a detection buffer containing lysis buffer as well as $^{125}$I-labeled cAMP tracer (NEN). After 3 hours of incubation at room temperature the bound radioactivity was determined in a liquid scintillation counter (TopCount-Packard Instruments). Basal activity (100% inhibition) was determined using the DMSO control while 0% inhibition was defined at the amount of pmol cAMP produced by 250 pM glucagon. The resulting amount of cAMP generated per compound dose was back-calculated from a cAMP standard curve based on the percent inhibition achieved at each dose. The calculated cAMP levels were plotted versus compound dose to obtain IC$_{50}$ values using non-linear four-parameter curve fitting with Assay Data Analyzer software (Merck & Co., Inc.).

Certain embodiments of the invention have been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:
1. A compound represented by formula I:

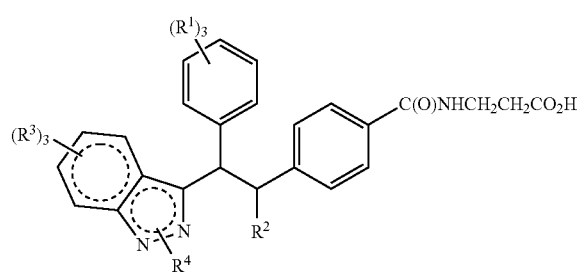

or a pharmaceutically acceptable salt thereof wherein:
each $R^1$ represents H or is selected from: halo, CN, OH, NO$_2$, CO$_2$R$^a$, NR$^a$R$^b$, S(O)$_p$R$^a$, C$_{1-10}$alkyl, C$_{2-10}$alkenyl or C$_{1-10}$alkoxy, the alkyl and alkenyl portions of C$_{1-10}$alkyl, C$_{2-10}$alkenyl and C$_{1-10}$alkoxy being optionally substituted with 1-5 halo atoms up perhalo; and further optionally substituted with 1 group selected from: OH, oxo or C$_{1-6}$alkoxy;

p represents 0, 1 or 2;

each R$^a$ and R$^b$ independently represents H or C$_{1-4}$alkyl optionally substituted with 1-5 halo atoms up to perhalo; and further optionally substituted with 1 group selected from: OH, oxo or C$_{1-6}$alkoxy;

R$^2$ represents C$_{1-6}$alkyl or C$_{2-6}$alkenyl, each optionally substituted with 1-5 halo atoms up to perhalo, and further optionally substituted with 1 group selected from: OH, oxo or C$_{1-6}$alkoxy:

each R$^3$ represents H or halo, or 1-2 R$^3$ groups represent H or halo and the remainder represent a member selected from: CN, OH, NO$_2$, CO$_2$R$^a$, NR$^a$R$^b$, S(O)$_p$R$^a$, phenyl or 5-6 membered heteroaryl containing 1-3 nitrogen atoms and 0-1 oxygen or sulfur atoms, said phenyl and heteroaryl being optionally substituted with 1-3 halo atoms and 1-2 members selected from: S(O)$_p$R$^a$, C$_{1-3}$alkyl, C$_{1-3}$alkoxy, haloC$_{1-3}$alkyl, haloC$_{1-3}$alkoxy, C$_{1-10}$alkyl, C$_{2-10}$alkenyl or C$_{1-10}$alkoxy, the alkyl and alkenyl portions of C$_{1-10}$alkyl, C$_{2-10}$alkenyl and C$_{1-10}$alkoxy being optionally substituted with 1-5 halo atoms up to perhalo; and further optionally substituted with 1 group selected from: OH, oxo, NR$^a$R$^b$, or C$_{1-6}$alkoxy;

and R$^4$ represents H or is selected from: C$_{1-4}$alkyl, haloC$_{1-4}$alkyl, phenyl optionally substituted with 1-3 halo groups and 1-2 C$_{1-3}$alkyl; haloC$_{1-3}$alkyl, OC$_{1-3}$alkyl or haloC$_{1-3}$alkyl groups.

2. A compound accordance with claim 1, or a pharmaceutically acceptable salt thereof, wherein:

each R$^1$ represents H or is selected from: halo, CN, C$_{1-10}$alkyl, or C$_{1-10}$alkoxy, the alkyl portions of C$_{1-10}$alkyl and C$_{1-10}$alkoxy being optionally substituted with 1-5 halo atoms up to perhalo; and further optionally substituted with 1 group selected from: OH; oxo or C$_{1-6}$alkoxy.

3. A compound in accordance with claim 2, or a pharmaceutically acceptable salt thereof, wherein:

each R$^1$ represents H or is selected from: halo selected from chloro or fluoro, CN, C$_{1-4}$alkyl, or C$_{1-4}$alkoxy, the alkyl portions of C$_{1-4}$alkyl and C$_{1-4}$alkoxy being optionally substituted with 1-3 halo atoms selected from: chloro or fluoro; and further optionally substituted with 1 group selected from: OH or OCH$_3$.

4. A compound in accordance with claim 3, or a pharmaceutically acceptable salt thereof, wherein:

each R$^2$ represents H or is selected from: halo selected from: chloro or fluoro, or CN.

5. A compound in accordance with claim 1, or a pharmaceutically acceptable salt thereof, wherein:

R$^2$ represents C$_{1-3}$alkyl or C$_{2-4}$alkenyl, each optionally substituted with 1-3 halo atoms selected from; chloro or fluoro; and further optionally substituted with 1 group selected from OH, oxo, or OCH$_3$.

6. A compound in accordance with claim 5, or a pharmaceutically acceptable salt thereof, wherein:

R$^2$ represents n-propyl or alkyl, each optionally substituted with 1-3 halo atoms selected from: chloro or fluoro.

7. A compound in accordance with claim 6, or a pharmaceutically acceptable salt thereof, wherein:

R$^2$ represents n-propyl or allyl.

8. A compound in accordance with claim 1, or a pharmaceutically acceptable salt thereof, wherein:

each R$^3$ represents H or halo, or 1-2 R$^3$ groups represent H or halo and the remainder represent a member selected from CN, S(O)$_p$R$^a$, phenyl or 5-6 membered heteroaryl containing 1-3 nitrogen atoms and 0-1 oxygen or sulfur atom, said phenyl and heteroaryl being optionally substituted with 1-3 halo atoms and 1-2 members selected from S(O)$_p$R$^a$, C$_{1-3}$alkyl, C$_{1-3}$alkoxy, C$_{1-3}$alkyl, haloC$_{1-3}$alkoxy, C$_{1-10}$alkyl or C$_{1-10}$alkoxy, the alkyl portions of C$_{1-10}$alkyl and C$_{1-10}$alkoxy being optionally substituted with 1-3 halo atoms up to perhalo;

p is 0 or 2, and

R$^a$ is H or C$_{1-4}$alkyl optionally substituted with 1-3 halo atoms.

9. A compound in accordance with claim 8, or a pharmaceutically acceptable salt thereof, wherein:

each R$^3$ represents H or halo selected from: chloro, fluoro or bromo, or 1-2 R$^3$ groups represent H or halo selected from: chloro, fluoro or bromo and the remainder represent a member selected from: CN, C$_{1-4}$alkyl or C$_{1-4}$alkoxy, the alkyl and portions of C$_{1-4}$-alkyl and C$_{1-4}$alkoxy being optionally substituted with 1-3 halo atoms selected from: chloro or fluoro, SO$_2$C$_{1-4}$alkyl, phenyl or 5-6 membered heteroaryl containing 1-2 nitrogen atoms, said phenyl and heteroaryl being optionally substituted with 1-3 halo atoms selected from: chloro, fluoro or bromo and 1 member selected from: SO$_2$-C$_{1-3}$alkyl, C$_{1-3}$alkyl, C$_{1-3}$alkoxy, haloC$_{1-3}$alkyl or haloC$_{1-3}$alkoxy.

10. A compound in accordance with claim 9, or a pharmaceutically acceptable salt thereof, wherein:

each R$^3$ represents H or halo selected from: chloro or fluoro, or 1-2 R$^3$ groups represent H or halo selected from chloro and fluoro and the remainder represent a member selected from: bromo, CH$_3$, CF$_3$, CN, phenyl or pyridyl, said phenyl and pyridyl being optionally substituted with 1-2 halo atoms selected from: chloro or fluoro and 1 member selected from CH$_3$, OCH$_3$, CF$_3$, OCF$_3$ or SO$_2$CH$_3$.

11. A compound in accordance with claim 1, or a pharmaceutically acceptable salt thereof, wherein:

R$^4$ represents H or is selected from: C$_{1-3}$alkyl, haloC$_{1-3}$alkyl or phenyl optionally substituted with 1-3 halo groups selected from: chloro or fluoro and 1-2 C$_{1-2}$alkyl, CF$_3$, OCH$_3$ or OCF$_3$ groups.

12. A compound in accordance with claim 1, represented by formula I:

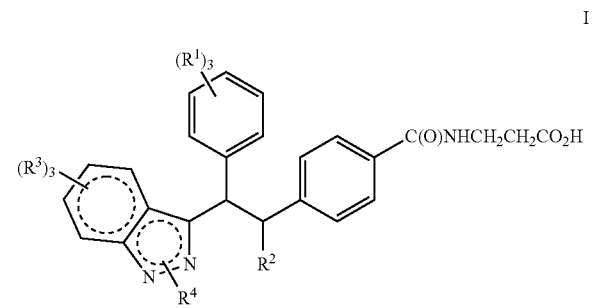

or a pharmaceutically acceptable salt thereof, wherein:

each R$^1$ represents H or is selected from halo, CN, C$_{1-10}$alkyl or C$_{1-10}$alkoxy, the alkyl portions of C$_{1-10}$alkyl and C$_{1-10}$alkoxy being optionally substituted with 1-5 halo atoms up to perhalo; and further optionally substituted with 1 group selected from: OH, oxo or C$_{1-6}$alkoxy;

$R^2$ represents $C_{1-3}$alkyl or $C_{2-4}$alkenyl, each optionally substituted with 1-3 halo atoms selected from: chloro or fluoro; and further optionally substituted with selected from: OH, oxo or $OCH_3$;

each $R^3$ represents H or halo, or 1-2 $R^3$ groups represent H or halo and the remainder represent a member selected from: CN, $S(O)_pR^a$, phenyl or 5-6 membered heteroaryl containing 1-3 nitrogen atoms and 0-1 oxygen or sulfur atom, said phenyl and heteroaryl being optionally substituted with 1-3 halo atoms and 1-2 members selected from: $S(O)_pR^a$, $C_{1-3}$alkyl, $C_{1-3}$alkoxy, halo$C_{1-3}$alkyl, halo$C_{1-3}$alkoxy, or $C_{1-10}$alkoxy, the alkyl portions of $C_{1-10}$alkyl and $C_{1-10}$alkoxy being optionally substituted with 1-3 halo atoms up to perhalo;

p is 0 or 2;

$R^a$ is H or $C_{1-4}$alkyl optionally substituted with 1-3 halo atoms; and $R^4$ represents H or is selected from: $C_{1-3}$alkyl, halo-$C_{1-3}$alkyl or phenyl optionally substituted with 1-3 halo groups selected from: chloro or fluoro and 1-2 $C_{1-2}$alkyl, $CF_3$, $OCH_3$ or $OCF_3$ groups.

13. A compound in accordance with claim 1, selected from the following:

EXAMPLE 1

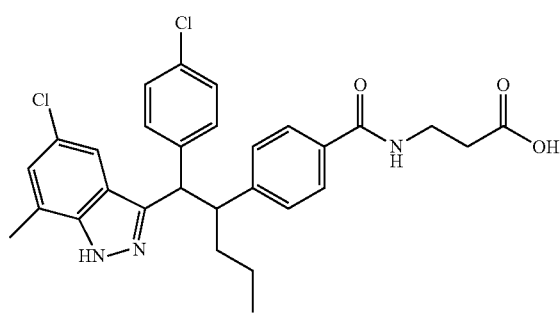

EXAMPLE 2

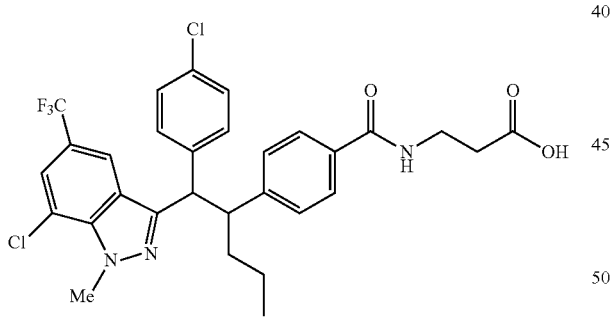

EXAMPLE 3

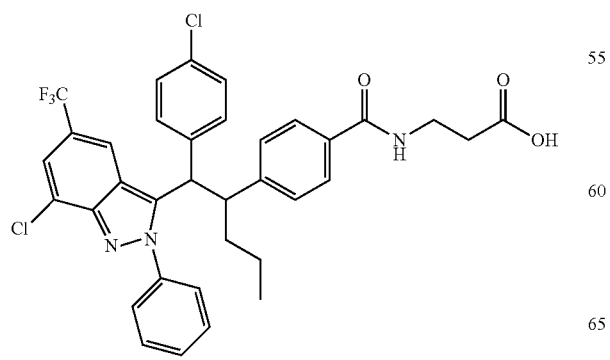

EXAMPLE 4

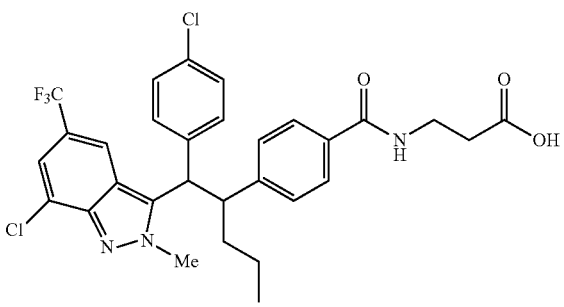

EXAMPLE 21

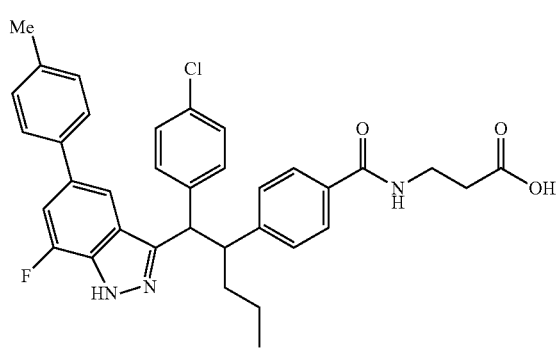

EXAMPLE 36

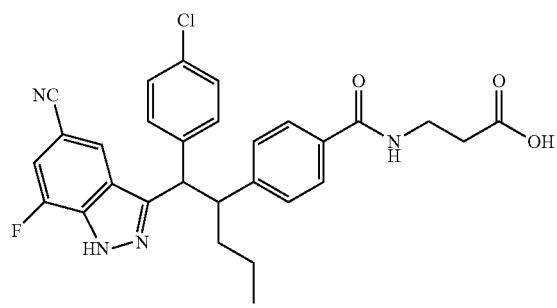

EXAMPLE 37

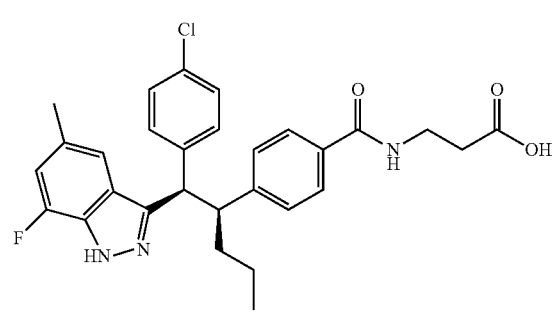

TABLE 1
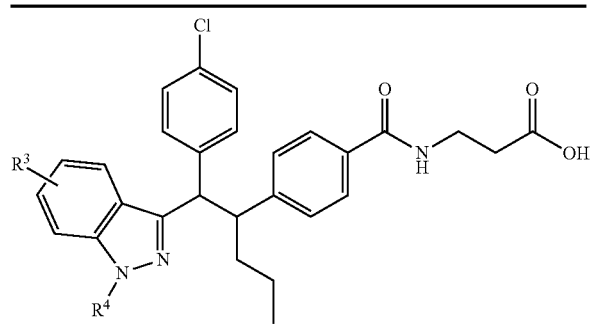
| EXAMPLE | R³ | R⁴ |
|---|---|---|
| 5 | 5-CF₃ | H |
| 6 | 5-CF₃, 7-Cl | H |
| 7 | 5-F, 7-F | H |
| 8 | 5-Cl, 7-Cl | H |
| 9 | 5-CF₃ | Me |
| 10 | 5-F, 7-F | Me |
| 11 | 5-Cl, 7-Me | Me |
| 12 | 5-Cl, 7-Cl | Me |
TABLE 2
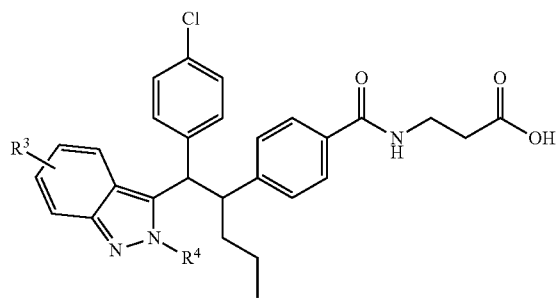
| EXAMPLE | R³ | R⁴ |
|---|---|---|
| 13 | 5-CF₃ | Me |
| 14 | 5-CF₃, 7-Cl | Et |
| 15 | 5-CF₃, 7-Cl | n-Pr |
| 16 | 5-CF₃, 7-Cl | i-Pr |
| 17 | 5-CF₃, 7-Cl | —CH₂CF₃ |
| 18 | 5-F, 7-F | Me |
| 19 | 5-Cl, 7-Cl | Me |
| 20 | 5-Cl, 7-Me | Me |
TABLE 3
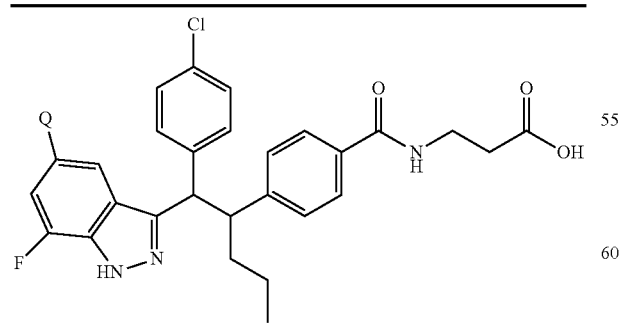
| EXAMPLE | Q |
|---|---|
| 22 | Br |
| 23 | H |
TABLE 3-continued
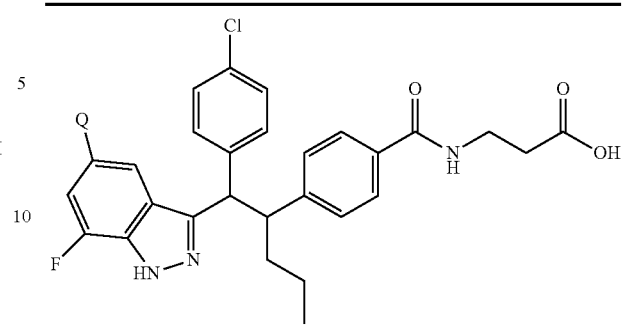
| EXAMPLE | Q |
|---|---|
| 24 | 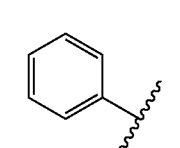 |
| 25 | 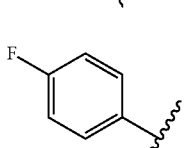 |
| 26 | 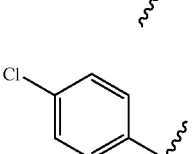 |
| 27 | 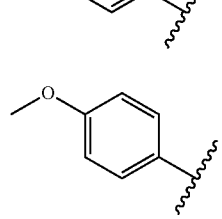 |
| 28 | 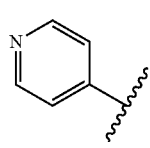 |
| 29 | 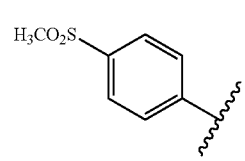 |
| 30 | 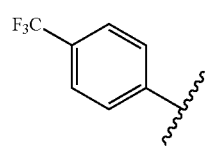 |
| 31 |  |

TABLE 3-continued

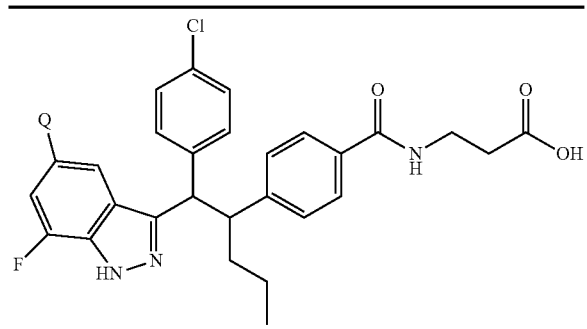

| EXAMPLE | Q |
|---|---|
| 32 | 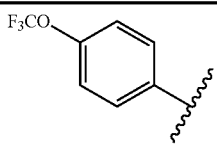 |
| 33 | 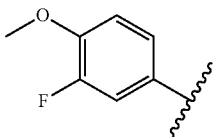 |
| 34 | 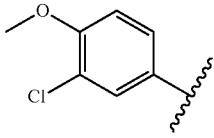 |
| 35 | 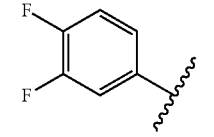 | or a pharmaceutically acceptable salt thereof.

14. A pharmaceutical composition comprising a compound in accordance with claim 1, or a pharmaceutically acceptable salt thereof, in combination with a pharmaceutically acceptable carrier.

15. A pharmaceutical composition in accordance with claim 14 further comprised of a member selected from: simvastatin, mevastatin, ezetimibe, atorvastatin, metformin, sibutramine, orlistat, Qnexa® (Vivus, inc. Mountain View, Calif.), topiramate, naltrexone, bupriopion, phentermine, losartan, hydrochlorothiazide, buformin, phenformin, troglitazone, pioglitazone, rosiglitazone, insulin, somatostatin, voglibose, miglitol, acarbose, sitagliptin, vildagliptin, saxagliptin, alogliptin, acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide, repaglinide, rimonabant or taranabant.

16. A method of treating type 2 diabetes mellitus in a mammalian patient in need of such treatment comprising administering to said patient a compound in accordance with claim 1 or a pharmaceutically acceptable salt thereof in an amount that is effective to treat said type 2 diabetes mellitus.

17. A method of delaying the onset of type 2 diabetes mellitus in a mammalian patient in need thereof comprising administering to the patient a compound in accordance with claim 1 or a pharmaceutically acceptable salt thereof in an amount that is effective to delay the onset of said type 2 diabetes mellitus.

18. A method of treating hyperglycemia, diabetes or insulin resistance in a mammalian patient in need of such treatment which comprises administering to said patient an effective amount of a compound in accordance with claim 1 or a pharmaceutically acceptable salt thereof.

19. method of treating non-insulin dependent diabetes mellitus in a mammalian patient in need of such treatment comprising administering to the patient an anti-diabetic effective amount of a compound in accordance with claim 1 or a pharmaceutically acceptable salt thereof.

20. A method in accordance with claim 16 further comprising administering to the patient a compound selected from: simvastatin, mevastatin, ezetimibe, atorvastatin, sibutramine, orlistat, Qnexa® (Vivus, Inc Mountain View, Calif.), topiramate, naltrexone, bupriopion, phentermine, losartan, hydrochlorothiazide, buformin, metformin, phenformin, troglitazone, pioglitazone, rosiglitazone, insulin, somatostatin, voglibose, miglitol, acarbose, sitagliptin, vildagliptin, saxagliptin, alogliptin, acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide, repaglinide, rimonabant or taranabant.

* * * * *